United States Patent
Mandella et al.

(10) Patent No.: US 6,414,779 B1
(45) Date of Patent: Jul. 2, 2002

(54) INTEGRATED ANGLED-DUAL-AXIS CONFOCAL SCANNING ENDOSCOPES

(75) Inventors: Michael J. Mandella, Cupertino; Mark H. Garrett, Morgan Hill; Gordon S. Kino, Stanford, all of CA (US)

(73) Assignee: Opeical Biopsy Technologies, Inc., San Jose, CA (US)

( * ) Notice: Subject to any disclaimer, the term of this patent is extended or adjusted under 35 U.S.C. 154(b) by 36 days.

(21) Appl. No.: 09/728,566

(22) Filed: Nov. 30, 2000

(51) Int. Cl.$^7$ .............................................. G02B 26/08
(52) U.S. Cl. ...................... 359/212; 359/201; 359/202; 359/205; 359/208; 359/368; 359/372; 359/900; 385/83; 385/88
(58) Field of Search ................................ 359/201–205, 359/208, 212, 223–226, 368, 372, 373, 377, 385, 15, 17, 558, 563, 565, 572, 634, 900; 250/234, 578.1, 458.1, 459.1; 385/15, 19, 83, 88, 147; 600/160, 167; 606/18

(56) References Cited

U.S. PATENT DOCUMENTS

| 5,034,613 A | 7/1991 | Denk et al. ............... 250/458.1 |
| 5,120,953 A | 6/1992 | Harris ...................... 250/227.2 |

(List continued on next page.)

FOREIGN PATENT DOCUMENTS

DE  4326473  5/1997

OTHER PUBLICATIONS

Lindek et al., "Optical transfer functions for Confocal theta Fluorescence microscopy", J. Opt. Soc. Am. A, vol. 13, No. 3, Mar. 1996, pp. 479–482.

Stelzer et al., "Fundamental reduction of the observation volume in far–field light microscopy by detection orthogonal to the illumination axis: confocal theta microscopy", Optics Communications 111(1994), pp. 536–547. (No month).

(List continued on next page.)

Primary Examiner—James Phan
(74) Attorney, Agent, or Firm—Lumen Intellectual Property Services, Inc.

(57) ABSTRACT

The present invention provides a novel class of integrated angled-dual-axis confocal scanning endoscopes. An integrated angled-dual-axis confocal scanning endoscope according to the present invention advantageously exploits an angled-dual-axis confocal arrangement in a silicon micromachined and fiber-coupled construction, rendering it enhanced resolution, faster scanning, higher sensitivity, highly integrated and scalable structure. An integrated angled-dual-axis confocal scanning endoscope thus constructed can be readily miniaturized for many applications, such as in vivo imaging of biological specimens. One or two illumination beams may be employed in an angled-dual-axis confocal scanning endoscope of the present invention, thereby providing an assortment of reflectance and fluorescence images. An angled-dual-axis confocal scanning endoscope of the present invention is further capable of providing various line and cross-sectional-surface scans with fast speed and high precision. As such, the angled-dual-axis confocal scanning endoscopes of the present invention provide advantages of high-speed and versatile scanning, larger dynamic range of detection, larger field of view and longer working distance, a compact and integrated construction, and versatile imaging capabilities. These novel devices are particularly suitable for biological and medical imaging applications.

101 Claims, 12 Drawing Sheets

U.S. PATENT DOCUMENTS

| | | | | |
|---|---|---|---|---|
| 5,161,053 | A | 11/1992 | Dabbs | 359/384 |
| 5,969,854 | A | 10/1999 | Stelzer et al. | 359/385 |
| 5,973,828 | A | 10/1999 | Webb | 359/385 |
| 6,020,591 | A | 2/2000 | Harter et al. | 250/458.1 |
| 6,028,306 | A | 2/2000 | Hayashi | 250/235 |
| 6,057,952 | A | 5/2000 | Kubo et al. | 359/196 |
| 6,064,518 | A | 5/2000 | Stelzer et al. | 359/368 |
| 6,069,698 | A | 5/2000 | Ozawa et al. | 356/345 |
| 6,088,145 | A | 7/2000 | Dickensheets et al. | 359/196 |
| 6,351,325 | B1 * | 2/2002 | Mandella et al. | 359/210 |

OTHER PUBLICATIONS

Hell et al., "Far-field fluorescence microscopy with three-dimensional resolution in the 100-nm range", Journal of Microscopy, vol. 187, Pt. 1, Jul. 1997, pp. 1–7.

Stelzer et al., "A new tool for the observation of embryos and other large specimens: confocal theta fluorescence microscopy", Journal of Microscopy, vol. 179, Pt. 1, Jul. 1995 pp. 1–10.

Webb et al., "Confocal microscope with large field and working distance", Applied Optics vol. 38, No. 22, Aug. 1, 1999, pp. 4870–4875.

Sinzinger et al., "Planar optical Confocal microscope for imaging and sensing" European Optical Society Topical Meetings Digest Series, vol. 9, Engelberg, Switzerland, Apr. 19996, pp. 1–3.

Klug et al., "Implementation of multilens, micro-optical systems with large numerical aperture by stacking of microlenses", Applied Optics, vol. 38, No. 34, Dec. 1, 1999.

Beaurepaire et al., "Combined scanning optical coherence and two-photon-excited fluorescence microscopy", Optics Letters, vol. 24, No. 14, Jul. 1999, pp. 969–971.

Lakowicz et al., "Two-color Two-photon Excitation of Fluorescence", Photochemistry and Photobiology, 64(4), 1996, pp. 632–635. (No month).

Lindek et al., "Resolution improvement by nonconfocal theta microscopy", Optics Letters, vol. 24, No. 21, Nov. 1, 1999, pp. 1505–1507.

* cited by examiner

INTEGRATED ANGLED-DUAL-AXIS CONFOCAL SCANNING ENDOSCOPES

FIELD OF THE INVENTION

This invention relates generally to the field of confocal microscopes. In particular, it is related to a novel class of integrated, miniaturized, fiber-coupled, high-precision confocal scanning endoscopes that are particularly suitable for biomedical applications.

BACKGROUND ART

The advent of fiber optics and laser technology has brought a renewed life to many areas of conventional optics. Confocal microscopes, for example, have enjoyed higher resolution, more integrated structure, and enhanced imaging capability. Consequently, confocal microscopes have become increasingly powerful tools in a variety of applications, including biological and medical imaging, optical data storage and industrial applications.

In recent years, a great deal of ingenuity has accordingly been devoted to improving the axial resolution of confocal microscopes. A particularly effective approach is to spatially arrange two separate illumination and observation objective lenses, or illumination and observation beam paths, in such a way that the illumination beam and the observation beam intersect at an angle theta ($\theta$) at the focal points, so that the overall point-spread function for the microscope, i.e., the overlapping volume of the illumination and observation point-spread functions results in a substantial reduction in the axial direction. A confocal microscope with such an angled, dual-axis design is termed a confocal theta microscope, or an angled-dual-axis confocal microscope, hereinafter. Its underlying theory is described below for the purpose of elucidating the principle of the present invention. A more detailed theory of the confocal theta microscopy can be found in U.S. Pat. No. 5,973,828; by Webb et al. in "Confocal microscope with large field and working distance", Applied Optics, Vol.38, No.22, pp.4870; and by Stelzer et al. in "A new tool for the observation of embryos and other large specimens: confocal theta fluorescence microscopy", Journal of Microscopy, Vol.179, Part 1, pp. 1; all incorporated by reference.

The region of the point-spread function of a confocal microscope's objective that is of most interest is the region in which the point-spread function reaches its maximum value. This region is referred to as the "main lobe" of the point-spread function in the art. It is typically characterized in three dimensions by an ellipsoid, which extends considerably further in the axial direction than in the transverse direction. This characteristic shape is the reason that the axial resolution is inherently poorer than the transverse resolution in a conventional confocal microscope. When the main lobes of the illumination and observation point-spread functions are arranged to intersect at an angle in a confocal theta microscope, however, a predominantly transverse and therefore narrow section from one main lobe is made to multiply (i.e., zero out) a predominantly axial and therefore long section from the other main lobe. This synergistic multiplication of the two point-spread functions reduces the length of the axial section of the overall point-spread function, thereby enhancing the overall axial resolution.

This enhancement of axial resolution is even more dramatic when this technique is used with relatively low numerical aperture (NA) lenses. The shape of the overall point-spread function can be further adjusted by varying the angle at which the main lobes of the illumination and observation point-spread functions intersect.

In addition to achieving higher resolution, an angled-dual-axis confocal microscope described above renders a number of additional important advantages. For instance, since the observation beam is positioned at an angle relative to the illumination beam, scattered light along the illumination beam does not easily get passed into the observation beam, except in the region where the beams overlap. This substantially reduces scattered photon noise in the observation beam, thus enhancing the sensitivity and dynamic range of detection. Moreover, the illumination and observation beams do not become overlapping until very close to the focus—this effect is particularly prominent when using low NA focusing elements (or lenses) for focusing the illumination and observation beams. Therefore, such an arrangement prevents scattered light in the illumination beam from directly "jumping" to the corresponding observation beam, thereby further filtering out scattered photon noise in the observation beam. As such, an angled-dual-axis confocal microscope has much lower noise and is capable of providing much higher contrast when imaging in a scattering medium, rendering it highly suitable for imaging within biological specimens.

Furthermore, in recent years optical fibers have been used in confocal systems to transmit light more flexibly. A single-mode fiber is typically used so that an end of the fiber is also conveniently utilized as a pinhole for both light emission and detection. This arrangement is not susceptible to the alignment problems the mechanical pinholes in the prior art systems tend to suffer. Moreover, the use of optical fibers enables the microscopes to be more flexible and compact in structure, along with greater maneuverability in scanning.

The aforementioned angled-dual-axis confocal arrangement can be further utilized to perform two-photon (and multi-photon) fluorescence microscopy, so as to exploit its high resolution and low noise capabilities. Two-photon (and multi-photon) fluorescence microscopy has been described and performed in the art, as exemplified by Lakowicz et al. in "Two-color Two-Photon Excitation of Fluorescence", Photochemistry and Photobiology, 64(4), (1996) pp.632–635; by Beaurepaire et al. in "Combined scanning optical coherence and two-photon-excited fluorescence microscopy", Optics Letters, Vol.24, No.14, (1999) pp.969–971; and by Lindek et al. in "Resolution improvement in nonconfocal theta microscopy", Optics Letters, Vol.24, No.21, (1999) pp.1505–1507. In such an arrangement, two illumination beams are directed to intersect optimally, such that each of the two observation beams thus produced is in an optimal confocal arrangement with its corresponding illumination beam. Whereas traditional single-photon fluorescence laser microscopy requires only a single photon $\lambda_3$ for excitation, two-photon fluorescence microscopy requires simultaneous absorption of two photon $\lambda_1$ and $\lambda_2$ for excitation. In terms of energy, $hc/\lambda_3 = hc/\lambda_1 + hc/\lambda_2$. Thus, $\lambda_1$ and $\lambda_2$ are both longer in wavelength than $\lambda_3$. However, it is important to note that $\lambda_2$ need not necessarily equal $\lambda_1$. Indeed, any combination of wavelengths can be used, so long as the net energy requirements for exciting a particular type of fluorophores are satisfied. Accordingly, two-photon (or multi-photon) fluorescence microscopy has been used in the art for imaging various types of fluorophores (or fluorophore indicators attached to proteins and biological cells) that are of particular interest to biomedical applications.

The past few years have seen a number of confocal theta microscopes in the art for performing scanning reflectance and fluorescence microscopy, as exemplified by German Patent DE-OS 43 26 473 A1; by Webb et al. in "Confocal microscope with large field and working distance", Applied Optics, Vol.38, No.22, pp.4870; by U.S. Pat. No. 5,973,828 of; by U.S. Pat. No. 6,064,518 of; by U.S. Pat. No. 5,034,613 of Denk et al.; and by U.S. Pat. No. 6,020,591 of Harter et al. None of these prior art confocal systems, however, perform the scanning microscopy in an angled-dual-axis confocal arrangement that is easily scalable to a small size instrument. Moreover, the designs of these prior art confocal systems are such that they do not lend these systems to be miniaturized confocal scanning endoscopes, suitable for biomedical imaging and other applications where relatively long working distance, large field of view, high resolution, fast scanning, and highly compact and maneuverable imaging tools are required.

Hence, there is a need in the art for a miniaturized confocal scanning endoscope that provides high resolution, fast scanning, high sensitivity, and versatile imaging capabilities.

SUMMARY OF THE INVENTION

The aforementioned need in the art is provided by a novel class of integrated angled-dual-axis confocal scanning endoscopes according to the present invention. An integrated angled-dual-axis confocal scanning endoscope of the present invention advantageously exploits the benefits of using relatively low NA objectives and a "post-objective" scanning means in an angled-dual-axis confocal arrangement, and a silicon micro-machined and fiber-coupled construction. The integrated angled-dual-axis confocal scanning endoscope thus constructed provides sufficient resolution, working distance, field of view, scanning speed and sensitivity suitable for biological imaging in a highly integrated and compact structure, rendering it further adaptable to an in-vivo imaging endoscope. One or two illumination beams may be employed in the angled-dual-axis confocal scanning endoscope of the present invention, thereby providing an assortment of reflectance and fluorescence images. The angled-dual-axis confocal scanning endoscope of the present invention is further capable of providing a combination of line and surface scans with fast speed and high precision.

The present invention provides a micro-machined angled-dual-axis confocal scanning endoscope, comprising a silicon substrate, a scanning mirror means mechanically coupled to the substrate, a silicon spacer containing a cavity, a base-plate carrying first and second reflective focusing elements along with an optical window, and first and second optical fibers. The cavity is disposed between the scanning mirror means and the optical window. The cavity is typically produced in the silicon spacer by way of anisotropical etching known in the art of silicon fabrication technology for producing cavities in silicon structure. The cavity thus produced comprises first and second side-walls that are positioned with predetermined and precise orientations, and also bear first and second V-grooves respectively. First and second optical fibers pass through the first and second side-walls by way of the first and second V-grooves, such that each of the first ends of the first and second optical fibers is in direct optical communication with the cavity. The inner surfaces of the first and second side-walls provide first and second reflective surfaces, each with a precise and predetermined orientation, as determined by the well-known crystal structure of silicon and the way of etching taking place in silicon. The first and second reflective focusing elements are generally selected from the group consisting of diffractive optical elements, reflective diffraction lenses, holographic optical elements, reflective off-axis binary lenses, and curved mirrors. The scanning mirror means may be mechanically coupled to the substrate by way of a hinge means, which also provides a pivoting axis. The optical window in the base-plate is disposed adjacent to an object, so as to provide the passages of optical beams between the cavity and the object.

It should be noted that in this specification and appending claims, a scanning mirror means should be construed in a broad sense as including one or more scanning mirrors that can rotate about one or two axes, one or more assemblies of scanning mirrors along with appropriate mechanical/electrical coupling mechanisms that provide rotation about one or two axes, or other scanning means known in the art that can provide beam steering/scanning in one or two dimensions. For instance, a scanning mirror means may comprise a single scanning mirror (such as a silicon scanning micro-machined mirror), or an assembly of two (or more) scanning mirrors arranged such that they jointly provide rotation about one or two orthogonal axes. It can also comprise a gimbaled assembly of a scanning mirror and a frame which are configured to provide rotation about two orthogonal axes, or a combination of two (or more) such gimbaled assemblies. A skilled artisan can devise an appropriate scanning mirror means in accordance with the present invention, for a given application.

In operation, an illumination beam emerges from the first end of the first optical fiber and is directed onto the second reflective surface, which in turn deflects the illumination beam to the first reflective focusing element. The focused illumination beam is then passed onto and further directed by the scanning mirror means through the optical window to a first substantially diffraction-limited focal volume along a first optical axis within an object. Accordingly, an observation beam emanated from a second substantially diffraction-limited focal volume along a second optical axis within the object passes through the optical window into the cavity and is in turn collected by the scanning mirror means. The observation beam is then deflected onto the second reflective focusing element. The focused observation beam is further passed onto the first reflective surface, which in turn directs the observation beam to the first end of the second optical fiber. As such, the assembly of the first and second reflective surfaces along with the first and second reflective focusing elements constitutes an angled-dual-axis confocal focusing means in this case, which provides the first and second optical axes. The first and second optical axes are directed to intersect at an angle θ, such that the first and second focal volumes intersect synergistically at a confocal overlapping volume. The scanning mirror means further pivot the illumination and observation beams in such a way that the confocal overlapping volume of the beams moves through the object, thereby producing a scan.

In one embodiment of the present invention, the scanning mirror means comprises a single scanning mirror, which is substantially flat and can rotate about a pivoting axis. The scanning mirror pivots the illumination and observation beams jointly in such a way that the first and second focal volumes remain intersecting synergistically and that the confocal overlapping volume moves along an arc-line within the object, thereby producing an arc-line scan. Such an arc-line scan can also be obtained by using a scanning mirror means comprising two (smaller) scanning mirrors that are substantially co-planar and can co-rotate about a common pivoting axis. These mirrors can be operated in substantially synchronous motion, so as to scan illumination and observation beams in a way functionally equivalent to a single (larger) scanning mirror An advantage of using two smaller scanning mirrors is that faster scanning can be provided.

In another embodiment of the present invention, the scanning mirror means comprise two scanning mirrors that are substantially flat. The two scanning mirrors can rotate about their respective individual pivoting axes, which are substantially parallel. By counter-rotating relative to each other about the respective pivoting axes, the two scanning mirrors pivot the illumination and observation beams in such a way that the first and second focal volumes remain intersecting synergistically and that the confocal overlapping volume progressively deepens into the interior of the object along a vertical line, thereby producing a vertical-line scan.

In an alternative embodiment of the present invention, the scanning mirror means comprises a bi-axial scanning element capable of rotating about two orthogonal axes. Such a bi-axial scanning element can be provided by a gimbaled assembly of a scanning mirror and a frame, wherein the scanning mirror can rotate about a first pivoting axis and the frame along with the scanning mirror can rotate about a second pivoting axis. The first and second pivoting axes are configured to be substantially orthogonal. In this case, by rotating about either of the first or second pivoting axis, the scanning mirror pivots the illumination and observation beams jointly in such a way that the first and second focal volumes remain intersecting synergistically and that the confocal overlapping volume moves along an arc-line within the object, thereby producing an arc-line. Moreover, by rotating about both of the pivoting axes in a raster-scanning or other predetermined fashion, the scanning mirror can cause the confocal overlapping volume to move in a predetermined pattern along an arc-cross-sectional surface within the object, thereby producing an arc-cross-sectional-surface scan. For instance, by rotating the bi-axial scanning element about the first and second pivoting axes (where one pivoting axis provides a fast-scanning-axis and the other pivoting axis provides a slow-scanning-axis) in a raster-scanning manner, a successive sequence of arc-line scans along an arc-cross-sectional-surface can be produced.

In yet another embodiment of the present invention, the scanning mirror means comprises two bi-axial scanning elements, wherein each can be a gimbaled assembly as described above. The two bi-axial scanning elements are configured such that they can co-rotate about a common pivoting axis and thereby produce an arc-line scan, as in the case of a single scanning mirror described above. The two bi-axial scanning elements can further rotate about two individual pivoting axes that are substantially parallel and spaced apart. By counter-rotating relative to each other about the individual pivoting axes respectively, the bi-axial scanning elements can jointly cause the confocal overlapping volume to move in a predetermined pattern along a vertical-cross-sectional plane, thereby producing a vertical-cross-sectional scan. As a way of example, by first co-rotating about the common pivoting axis (fast-scanning-axis) and then counter-rotating about the respective individual axes (slow-scanning-axes) in a raster-scanning fashion, the two bi-axial scanning elements jointly cause the confocal overlapping volume to move in a successive sequence of arc-line scans that progressively deepen into the interior of the object along a vertical-cross-sectional plane. Alternatively, by first counter-rotating about the respective individual axes (fast-scanning-axes) and then co-rotating about the common pivoting axis (slow-scanning-axis) in a raster-scanning fashion, the two bi-axial scanning elements jointly cause the confocal overlapping volume to move in a successive sequence of radial-line scans, wherein each radial-line scan is angularly displaced relative to its adjacent radial-line scans in a fan-like pattern along a vertical-cross-sectional plane within the object.

It should be understood that when describing the intersection of the illumination and observation beams in this specification, the term "synergistic" means that the intersection of the first and second focal volumes (i.e., the main lobe of the illumination beam's point-spread function and the main lobe of the observation beam's point-spread function) is such that the resulting overlapping volume has comparable transverse and axial extents. This synergistic overlapping volume is termed "confocal overlapping volume" in this specification and appending claims. As such, the illumination beam intersects synergistically with the observation beam in the angled-dual-axis arrangement described above. Moreover, the observation beam described above should be construed in a broad sense as each carrying any light transmitted back from the object, including reflected light, scattered light, and fluorescent light of single-photon, two-photon, and multi-photon type.

A unique feature of the angled-dual-axis confocal scanning endoscope of the present invention is that the scanning mirror means is in direct optical communication with the angled-dual-axis focusing means and the object to be examined. This "post-objective" type of scanning technique enables the best on-axis illumination and observation point-spread functions to be utilized throughout the entire angular range of an arc-line scan, thereby providing greater resolution over a larger transverse field of view, while maintaining substantially diffraction-limited (or relatively aberration-free) performance. Such an arrangement is made possible by taking advantage of the longer working distance rendered by using relatively lower NA focusing elements in the angled-dual-axis focusing means.

Another important advantage of the angled-dual-axis arrangement of the present invention is that since the observation beam is positioned at an angle relative to its corresponding illumination beam, scattered light along the illumination beam does not easily get passed into the observation beam, except in the region where the beams overlap. This substantially reduces scattered photon noise in the observation beam, thus enhancing the sensitivity and dynamic range of detection. Moreover, by using low NA focusing elements in an angled-dual-axis confocal scanning endoscope of the present invention, the illumination and observation beams do not become overlapping until very close to the focus. Such an arrangement prevents scattered light in the illumination beam from directly "jumping" to the corresponding observation beam, thereby further filtering out scattered (or fluorescent) photon noise in the observation beam. Altogether, the angled-dual-axis confocal scanning endoscope of the present invention has much lower noise and is capable of providing much higher contrast when imaging in a scattering medium than the prior art confocal systems employing high NA lenses, rendering it highly suitable for imaging within biological specimens.

A further distinct advantage of the present invention is evident in the scalability of the angled-dual-axis confocal scanning endoscope, which allows for miniaturization while providing sufficient resolution, field of view, and working distance suitable for in-vivo imaging of biological specimens.

Two illumination beams can be employed in an angled-dual axis confocal scanning endoscope of the present invention, such as in any one of the embodiments described above. In this scenario, first and second illumination beams with first and second wavelengths emerge from the first ends of the first and second optical fibers respectively. The angled-dual-axis focusing means focuses and the scanning mirror means direct the two illumination beams through the optical window along the first and second optical axes, such that they intersect synergistically at a confocal overlapping volume within an object. First and second observation beams thus produced pass through the optical window into the cavity and are in turn collected along the second and first optical axes respectively by the scanning mirror means. The observation beams are then focused into the first ends of second and first optical fibers respectively by way of the angled-dual-axis focusing means. The scanning mirror means further pivot the first and second illumination beams (and thereby their corresponding observation beams) in such a way that the confocal overlapping volume of the beams moves through the object, thereby producing a scan. For instance, by utilizing various types of the scanning mirror means described above, arc-line scans, vertical-line scans, arc-cross-sectional-surface scans, and vertical-cross-sectional scans can be accordingly produced.

The aforementioned first and second illumination beams may have the same wavelength, for instance, in the infrared range. The fluorescence light thus produced would include one-color two-photon and multi-photon types of fluorescence. The first and second illumination beams may also have very different wavelengths. As a way of example, the first wavelength may be in the infrared range, while the second wavelength lies in the visible range. The fluorescence light thus obtained would include two-color two-photon (and possibly multi-photon) fluorescence. A skilled artisan will know how to selectively make use of a particular type of reflected and fluorescence light collected from the object and filter out spurious background light for a given application. (The filtering can be accomplished by way of band-pass filters, dichroic filters, wavelength-selective optical elements and the like, for instance).

In addition to collecting the first and second observation beams, a third observation beam comprising predominantly fluorescence light can be collected, providing an additional avenue for collection and detection of fluorescence light. The third observation beam can be collected by a third focusing element mounted on (or made to be an integral part of) the base-plate, such that it is in direct optical communication with the optical window. The third focusing element further focuses the third observation beam to an input end of a third optical fiber, which may be mechanically coupled to the substrate. It should be noted that the scanning mirror means is not involved in collecting the third observation beam in this case. The third optical fiber is preferably a multi-mode fiber of larger diameter (or made of a bundle of multiple optical fibers), so as to maximize the collection efficiency of light emanating from the confocal overlapping volume throughout its motion within the object during scanning. The first and second optical fibers are preferably single-mode fibers. Alternatively, an optical detector (such as a silicon photon detector) can be mounted on (or made to be an integral part of) the silicon substrate, so as to collect the third observation beam.

As such, an angled-dual-axis confocal scanning endoscope employing two illumination beams is capable of providing an assortment of reflectance and fluorescence images. For instance, a first wavelength-selective-beam-splitting means can be coupled to the first observation beam, diverting a portion of the first observation beam to a first optical detector. The first wavelength-selective-beam-splitting means can be configured to preferentially permit only the reflected light (characterized by a particular wavelength and bandwidth of light) carried by the first observation beam to pass through, thereby providing a first reflectance image signal.

A second wavelength-selective-beam-splitting means can be further coupled to the first observation beam, diverting an additional portion of the first observation beam to a second optical detector. The second wavelength-selective-beam-splitting means may be designed to preferentially permit only the particular wavelength and bandwidth of light corresponding to two-photon fluorescence light carried by the first observation beam to pass through, thereby providing a two-photon fluorescence image signal. Likewise, a third wavelength-selective-beam-splitting means can be coupled to the second observation beam, diverting a portion of the second observation beam to a third optical detector. The third wavelength-selective-beam-splitting means can be configured to preferentially permit only the reflected light (characterized by a particular wavelength and bandwidth of light) carried by the second observation beam to pass through, thereby providing a second reflectance image signal. And a fourth wavelength-selective-beam-splitting means may be further coupled to the second observation beam, providing an additional avenue for detecting the two-photon fluorescence light carried by the second observation beam, and so on. All in all, a cascade of the wavelength-selective-beam-splitter means can be optically coupled to either of the first and second observation beams, enabling various spectral components of each of the observation beams to be extracted and detected. Moreover, a superposition of reflectance and two-photon fluorescence images thus obtained would be highly desirable, for it provides complementary information about the morphology and functionality of a biological sample. It should be noted that it is possible to operate the present invention in a number of ways that would provide different combinations of reflectance and fluorescence (single-photon, two-photon, or multiple-photon) images, depending upon the instrument design and the types of light sources/wavelengths used. It is preferable to design the instrument in a way that maximizes the resolution of the images thus produced and contemporaneously minimizes the scattered and/or fluorescent photon noise in the image signal. This can be best accomplished by the following seven design rules, which insure that reflected or fluorescence light generated by each illumination beam is optimally collected only by its corresponding (angularly overlapping) observation beam:

1) In the case where the first observation beam is being used to collect reflectance image information characterized by a first wavelength, the second illumination beam should not include light with the first wavelength, and the first illumination beam must provide light with the first wavelength.

2) In the case where the first observation beam is being used to collect single-photon fluorescence image information characterized by a third wavelength when the object is excited by light of a second wavelength, the second illumination beam should not include single-photon excitation light with the second wavelength, and the first illumination beam should provide single-photon excitation light with the second wavelength.

3) In the case where the first observation beam is being used to collect one-color two-photon (1C2P) fluorescence image information characterized by a fifth wavelength when the object is excited by light of a fourth wavelength, the second illumination beam should not include 1C2P excitation light with the fourth wavelength, and the first illumination beam should provide 1C2P excitation light with the fourth wavelength.

4) In the case where either of the first and second observation beams, or both of the observation beams, are being used to collect two-color two-photon (2C2P) fluorescence image information characterized by an eighth wavelength when the object is excited by light that requires both of sixth and seventh wavelengths, the first and second illumination beams should each provide light with only one of the two required wavelengths, such that 2C2P excitation light is provided only in the region where the two illumination beams overlap both spatially and temporally.

5) In the case where the second observation beam is being used to collect reflectance image information characterized by a ninth wavelength, the first illumination beam should not include light with the ninth wavelength, and the second illumination beam must provide light with the ninth wavelength.

6) In the case where the second observation beam is being used to collect single-photon fluorescence image information characterized by an eleventh wavelength when the object is excited by light of a tenth wavelength, the first illumination beam should not include single-photon excitation light with the tenth wavelength, and the second illumination beam should provide single-photon excitation light with the tenth wavelength.

7) In the case where the second observation beam is being used to collect one-color two-photon (1C2P) fluorescence image information characterized by a thirteenth wavelength when the object is excited by light of a twelfth wavelength, the first illumination beam should not include 1C2P excitation light with the twelfth wavelength, and the second illumination beam should provide 1C2P excitation light with the twelfth wavelength.

The present invention further provides an angled-dual-axis confocal scanning system, comprising an angled-dual-axis confocal scanning endoscope of the present invention, first and second light sources, and first and second optical detectors. The first light source is optically coupled to a second end of the first optical fiber of the angled-dual-axis confocal scanning endoscope by way of a first wavelength-selective-beam-splitting element, providing the first illumination beam. The first wavelength-selective-beam-splitting element additionally diverts a portion of the second observation beam delivered by the first optical fiber to the first optical detector. Likewise, the second light source is optically coupled to a second end of the second optical fiber of the angled-dual-axis confocal scanning endoscope by way of a second wavelength-selective-beam-splitting element, providing the second illumination beam. The second wavelength selective beam-splitting element additionally diverts a portion of the first observation beam delivered by the second optical fiber to the second optical detector. By selecting appropriate first and second wavelength-selective-beam-splitting elements, various spectral components of the first and second observation beams can be extracted and detected according to the aforementioned design rules In the aforementioned angled-dual-axis confocal scanning system of the present invention, either of the first and second wavelength-selective-beam-splitting elements can be a dichroic filter, a wavelength division multiplexer (WDM), or a fiber-optic coupler. Each of the first and second light sources can be a continuous wave (CW) or pulsed light source, such as a fiber laser, a semiconductor laser, a diode pumped solid state laser, or other suitable fiber-coupled light source known in the art. The optical detector can be a PIN diode, an avalanche photo diode (APD), or a photomultiplier tube.

Such an angled-dual-axis confocal scanning system provides a simple and versatile imaging tool with high resolution and fast scanning capability.

All in all, the angled-dual-axis confocal scanning endoscopes of the present invention have advantages of higher resolution, faster scanning, higher sensitivity and larger dynamic range of detection, a larger field of view and a longer working distance, a compact and integrated construction, and contemporary reflectance and fluorescence imaging.

The novel features of this invention, as well as the invention itself, will be best understood from the following drawings and detailed description.

DETAILED DESCRIPTION

Although the following detailed description contains many specific details for the purposes of illustration, anyone of ordinary skill in the art will appreciate that many variations and alterations to the following details are within the scope of the invention. Accordingly, the exemplary embodiment of the invention described below is set forth without any loss of generality to, and without imposing limitations upon, the claimed invention.

Figure 1A:
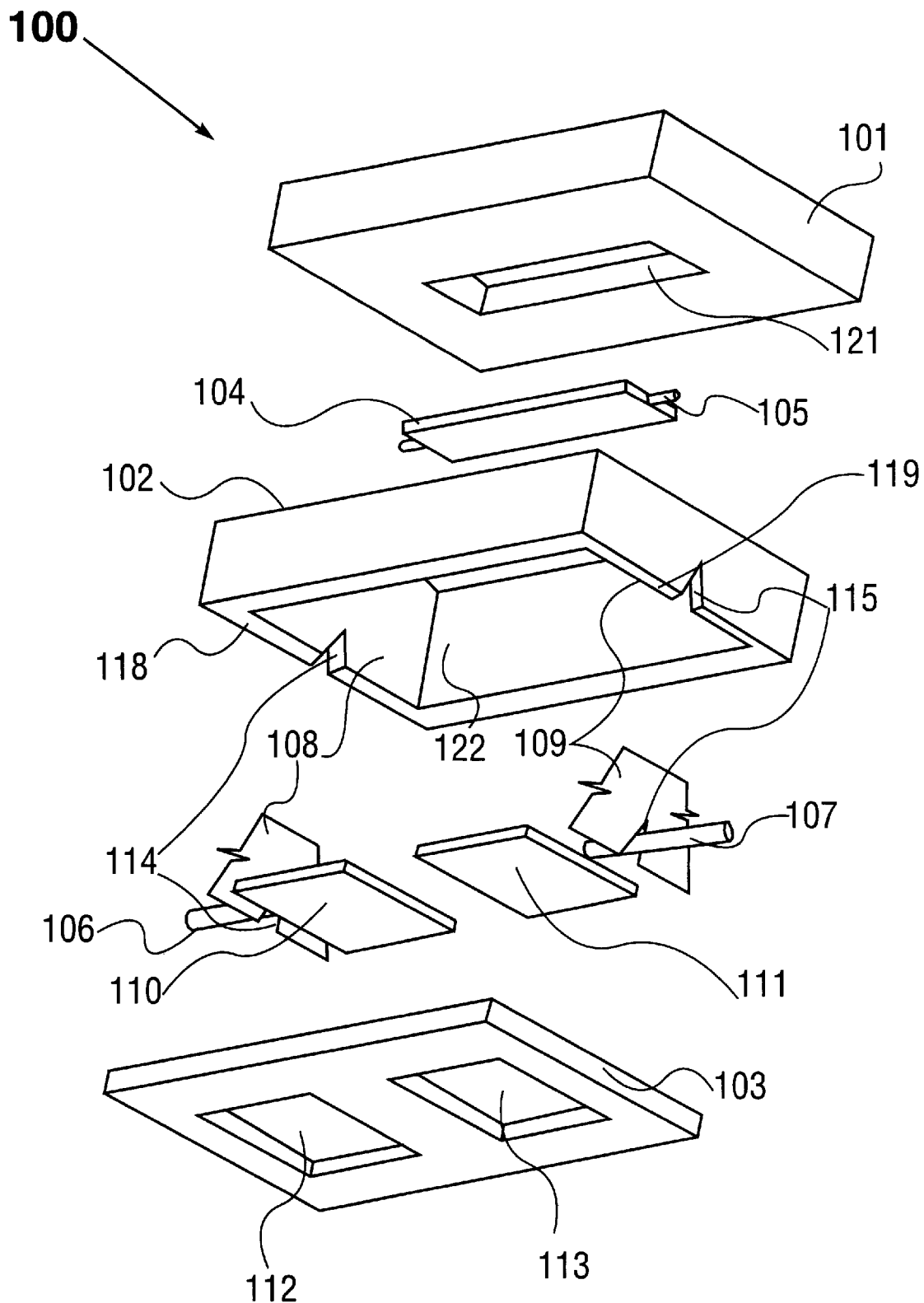
FIGS. 1A–1D show several views of an exemplary embodiment of a first integrated angled-dual-axis confocal scanning endoscope according to the present invention.

FIGS. 1A–1D depict several views of an exemplary embodiment of a first integrated angled-dual-axis confocal scanning endoscope according to the present invention. Depicted in FIG. 1A is an exploded view showing various parts of an integrated angled-dual-axis confocal scanning endoscope 100 of the present invention, produced by silicon micromachining technology. By way of example, angled-dual-axis confocal scanning endoscope 100 comprises a silicon substrate 101 containing a single dish-cavity 121; a scanning mirror means in the form of a micromachined scanning mirror 104; a silicon spacer 102 containing a cavity 122; first and second optical fibers 106, 107; first and second reflective beam-focusing elements 111, 110; and a base-plate 103 containing first and second pockets 113, 112. In an assembled configuration, scanning mirror 104 is disposed and suspended in dish-cavity 121 of silicon substrate 101 by a hinge-like element, which also provides a pivoting axis 105. First optical fiber 106 passes through a first side-wall 118 of cavity 122 by way of a first V-groove 114 etched into first side-wall 118, wherein the inner surface of first side-wall 118 serves as a first reflective surface 108. Likewise, second optical fiber 107 passes through a second side-wall 119 of cavity 122 by way of a second V-groove 115 etched into second side-wall 119, wherein the inner surface of second side-wall 119 provides a second reflective surface 109. Note that in this exemplary configuration first and second reflective surfaces 108, 109 are on the two opposing sides of cavity 122 and thereby facing each other. (It should be pointed out that first and second reflective surfaces 108, 109 need not necessarily be parallel to each other.) As such, first and second optical fibers 106, 107 approach cavity 122 from two opposing directions in an "anti-parallel" fashion. First and second pockets 112, 113 on base-plate 103 are configured to contain first and second reflective beam-focusing elements 111, 110.

Figure 1B:
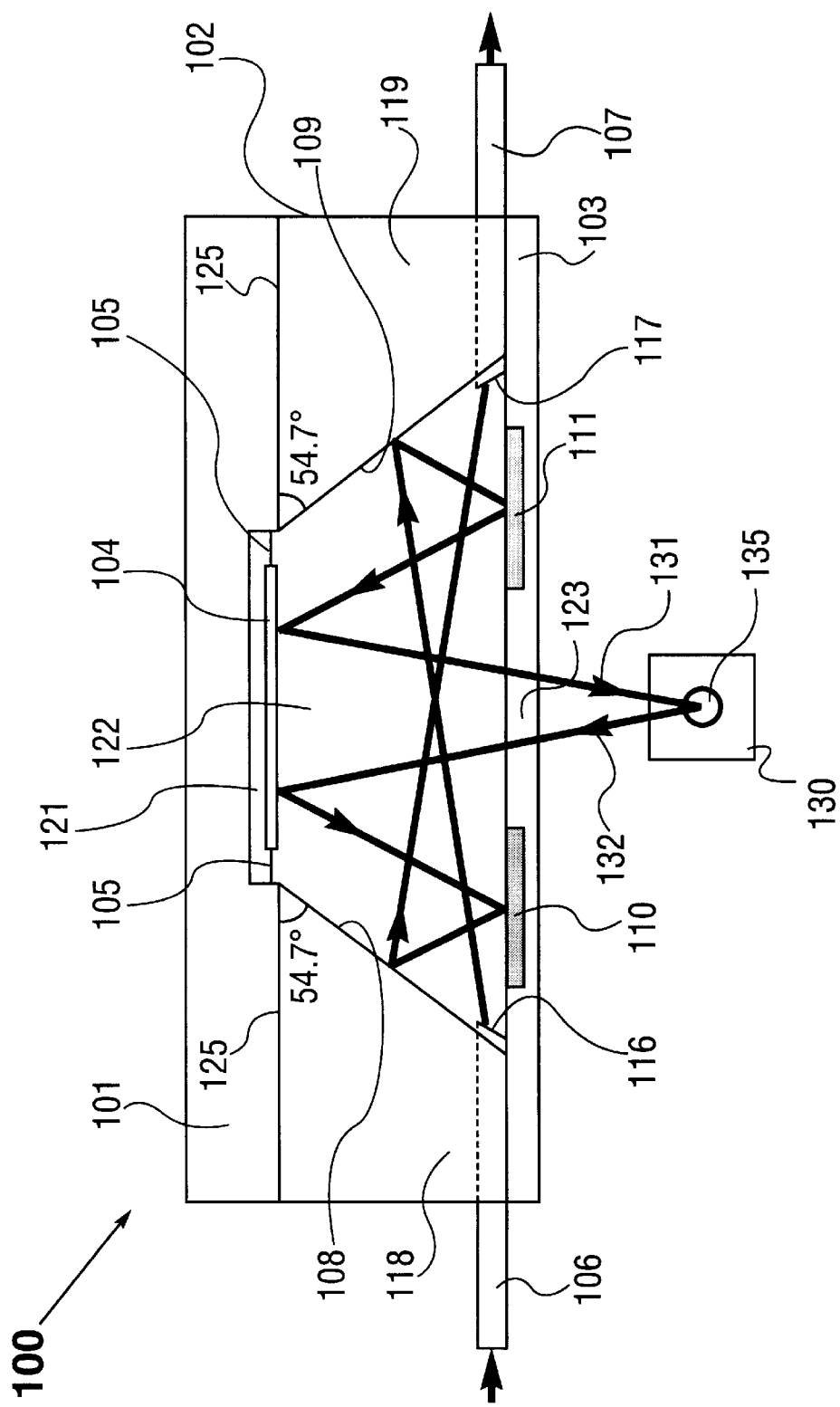

FIG. 1B shows a cross-sectional view of an assembled version of angled-dual-axis confocal endoscope 100 shown in FIG. 1A. Silicon spacer 102 is disposed between silicon substrate 101 and base-plate 103. Scanning mirror 104, being suspended in dish-cavity 121 by way of pivoting axis 105, is in direct optical communication with cavity 122 and optical window 123 in base-plate 103. Optical window 123 (not shown in FIG. 1A) may be a transparent region of base-plate 103, or mounted (or fused) onto base-plate 103, such that it is disposed between first and second reflective focusing elements 111, 110. First and second reflective focusing elements 111, 110 are mounted on base-plate 103 by way of being situated within first and second pockets 113, 112 (see FIG. 1A) respectively. First optical fiber 106 passes through first side-wall 118 of silicon spacer 102 (through first V-groove 114 shown in FIG. 1A), such that a first end 116 of first optical fiber 106 extends into and is in direct optical communication with cavity 122. Likewise, second optical fiber 107 passes through second side-wall 119 of silicon spacer 102 (through second V-groove 115 shown in FIG. 1A), such that a first end 117 of second optical fiber 107 extends into and is in direct optical communication with cavity 122.

FIG. 1B also provides an operational view of angled-dual-axis confocal endoscope 100 in an illustrative fashion. An illumination beam 131 emerges from first end 116 of first optical fiber 106 and is directed onto second reflective surface 109, which in turn deflects the beam to first reflective focusing element 111. The focused illumination beam is then passed onto and further directed by scanning mirror 104 through optical window 123 to a first substantially diffraction-limited focal volume (see FIG. 1C) within an object 130. Accordingly, an observation beam 132 emanated from a confocal overlapping volume 135 within object 130 passes through optical window 123 into cavity 122. Observation beam 132 is then collected by scanning mirror 104, and further deflected onto second reflective focusing element 110. The focused observation beam is then passed onto first reflective surface 108, which in turn directs the observation beam to first end 117 of second optical fiber 107.

Figure 1C:
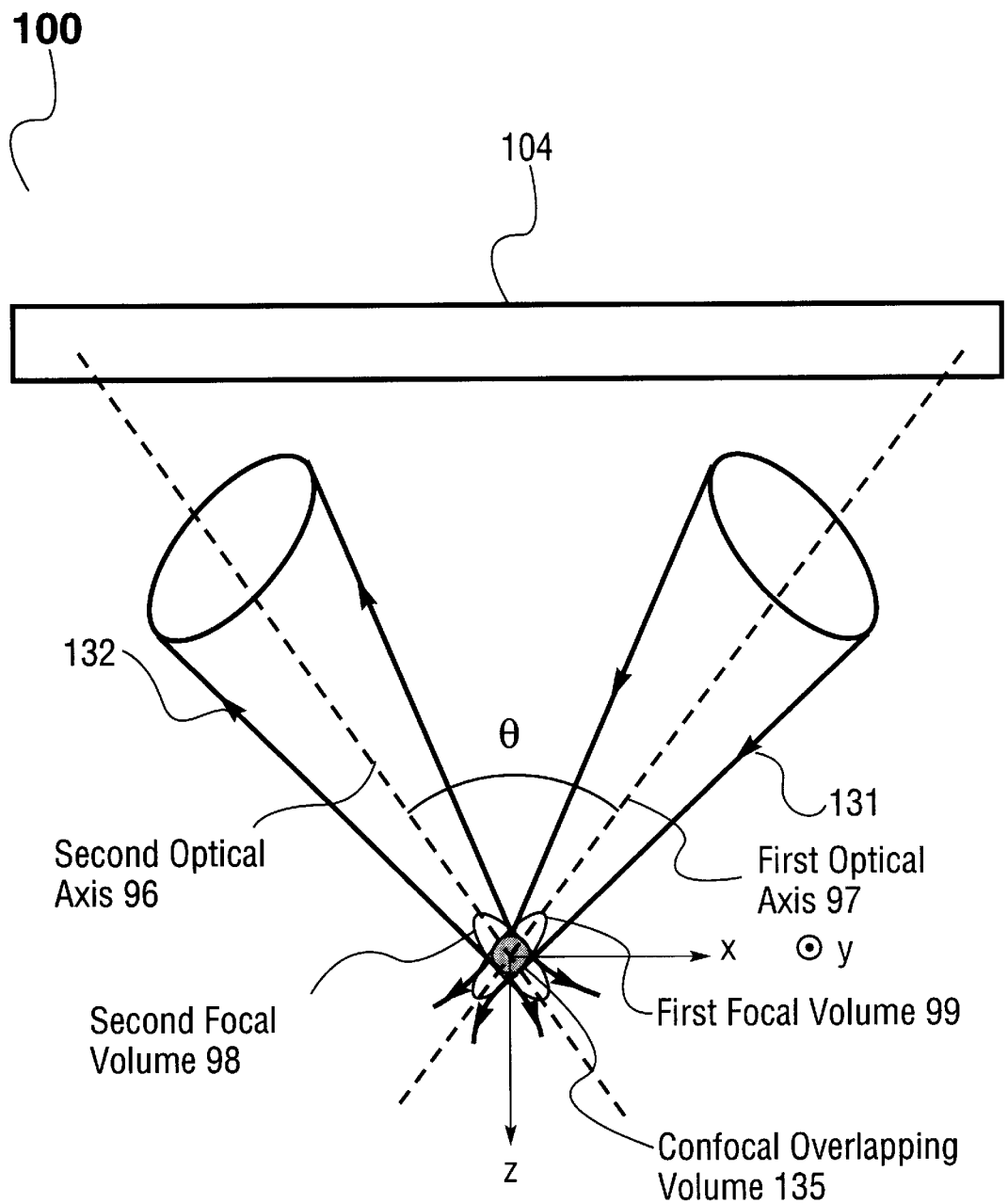

FIG. 1C provides a more detailed illustration of how illumination and observation beams 131, 132 are arranged to intersect within object 130 in FIG. 1B. Illumination beam 131, directed by scanning mirror 104, is focused to a first focal volume 99 oriented along a first optical axis 97 (within object 130 shown in FIG. 1B). Accordingly, observation beam 132 emanated from second focal volume 98 is directed along a second optical axis and received by scanning mirror 104. First and second optical axes 97, 96 are directed to intersect at an angle θ, such that first focal volume 99 and second focal volume 98 intersect synergistically at confocal overlapping volume 135. A three-dimensional x-y-z coordinate system is provided to describe the spatial extents of confocal overlapping volume 135, where the origin of the coordinate system is set at the center of confocal overlapping volume 135. The z-axis defines the axial (or vertical) direction, whereas x-axis and y-axis (pointing out of the page) represent two orthogonal transverse directions.

It should be noted that in this specification and appending claims, an observation beam should be construed in a broad sense as comprising any light transmitted back from the object, including reflected light, scattered light, and fluorescent light. A skilled artisan will know how to selectively make use of a particular type of light collected from the object and filter out spurious background light for a given application. (The filter can be accomplished by way of band-pass filters, dichroic filters, wavelength-selective optical elements, and the like.)

In the present invention, various optical elements are aberration-corrected, and single-mode optical fibers are preferably used to provide point light sources and detectors. Accordingly, first focal volume 99 and second focal volume 98 described above are preferably diffraction-limited, defined by the main lobes of the illumination beam's point-spread function and the observation beam's point-spread function. Confocal overlapping volume 135 is preferably diffraction-limited, determined by a synergistic overlapping of the main lobes of the illumination beam's point-spread function and the observation beam's point-spread function, as illustrated in FIG. 1C.

A skilled artisan will know how to carry out a model calculation to estimate the spatial extent of the confocal overlapping volume described above, hence the spatial resolution in three dimensions. As a way of example, for NA of beam-focusing elements (e.g., focusing mirrors) in the range of 0.2–0.3, the intersecting angle θ between 60-degree and 90-degree, and the wavelength of light near 1.3 $\mu$m, the corresponding axial resolution generally ranges from 2 to 3.5 $\mu$m, and the transverse resolution (in either x or y direction) typically ranges from 1.5 to 2.5 $\mu$m.

Figure 1D:
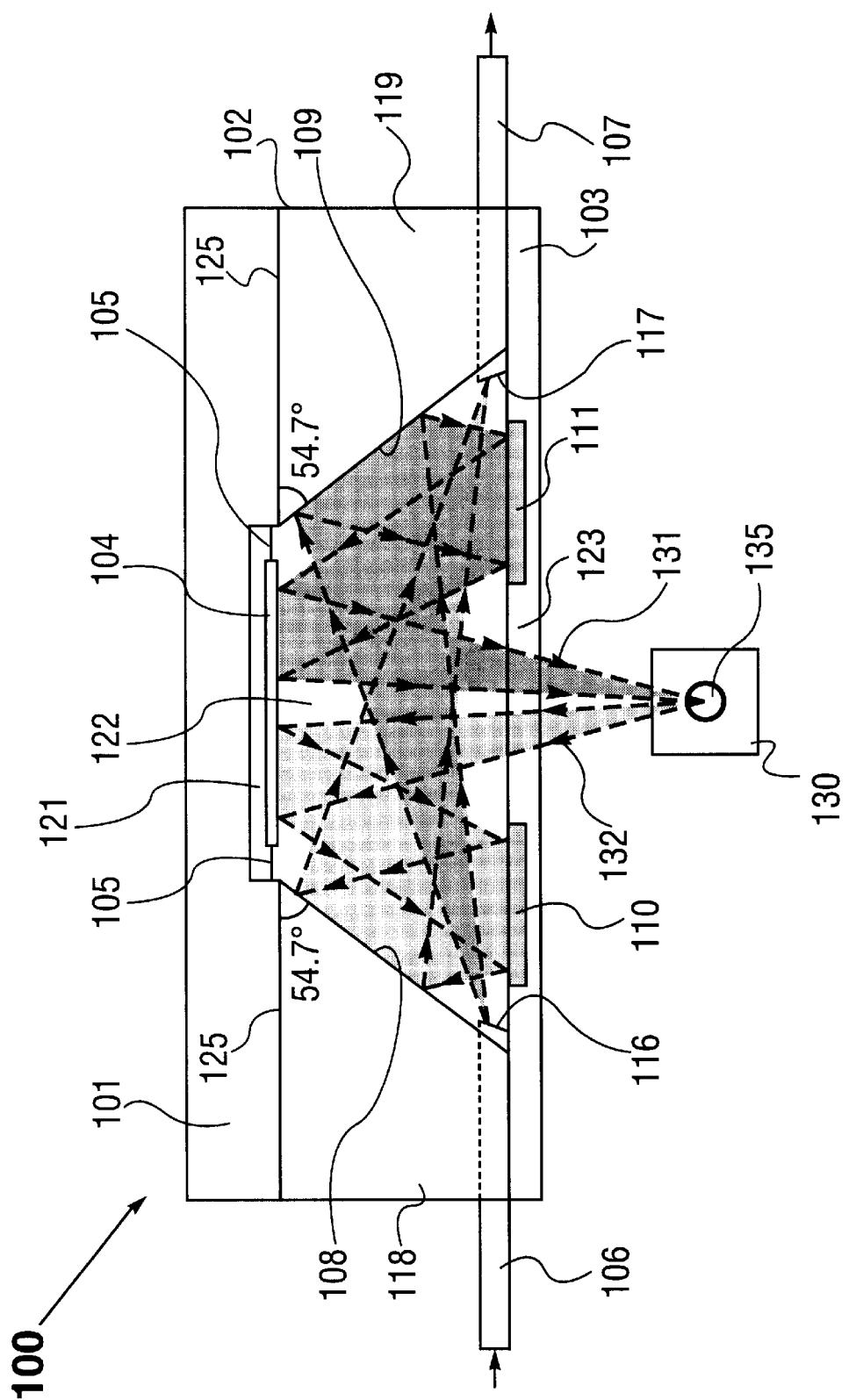

In view of the foregoing, FIG. 1D depicts another operational view of angled-dual-axis confocal endoscope 100 shown in FIG. 1B, providing a more detailed illustration of respective passages of illumination beam 131 and observation beam 132 inside cavity 122. It should be noted that the particular assembly of first and second reflective surfaces 108, 109 along with first and second reflective focusing elements 111, 110 constitutes an "angled-dual-axis focusing means" in this case, which provides first and second optical axes (see FIG. 1C) oriented in such a way that focused illumination and observation beams 131, 132 intersect at confocal overlapping volume 135 within object 130.

In the embodiment of FIG. 1B (or FIG. 1D), by rotating about pivoting axis 105, scanning mirror 104 is further capable of pivoting illumination beam 131 and observation beam 132 in such a way that illumination beam 131 and observation beam 132 remain intersecting at angle θ and that confocal overlapping volume 135 at the intersection of the two beams moves along an arc-line within object 130, thereby producing an arc-line scan.

An important characteristic of the arc-line scan described above is that the relative spatial orientation between illumination beam 131 and observation beam 132 stays fixed in the course of the entire scan, once the two beams are arranged to intersect in an optimal manner initially. Consequently, this "post-objective" way of beam scanning provided by angled-dual-axis confocal scanning endoscope 100 of the present invention is inherently of higher precision, faster speed, and larger field of view, in contrast to the conventional "pre-objective" way of beam scanning employed in the prior art systems (which use high NA and therefore short working distance lenses).

It should be noted that to achieve faster scanning, single scanning mirror 104 in the embodiment of FIGS. 1A–1B (or FIG. 1D) can be replaced by an assembly of two smaller co-planar scanning mirrors, such as two silicon micro-machined scanning mirrors. Owing to their unique fabrication process, these mirrors can be constructed to co-rotate about a common axis (such as pivoting axis 105) and operate in substantially synchronous motion, so as to scan illumination and observation beams in a way functionally equivalent to single scanning mirror 104.

It should be noted that in this specification and appending claims, a scanning mirror means should be construed in a broad sense as including one or more scanning mirrors that can rotate about one or two axes, one or more assemblies of scanning mirrors along with appropriate mechanical/electrical coupling mechanisms that provide rotation about one or two axes, or other scanning means known in the art that can provide beam steering/scanning in one or two dimensions. As exemplified in the aforementioned and following embodiments, a scanning mirror means may comprise a single scanning mirror (such as a silicon scanning micro-machined mirror), or an assembly of two (or more) scanning mirrors arranged such that they jointly provide rotation about one or two orthogonal axes. It can also comprise a gimbaled assembly of a scanning mirror and a frame which are configured to provide rotation about two orthogonal axes, or a combination of two (or more) such gimbaled assemblies. A skilled artisan can devise an appropriate scanning mirror means in accordance with the present invention, for a given application.

In the embodiment of FIGS. 1A–1B (or FIG. 1D), silicon substrate 101 with dish-cavity 121, and silicon spacer 102 along with cavity 122 can be constructed by way of the silicon fabrication technology known in the art. It is well known in the art that various V-grooves and cavities can be etched into silicon in a very precise manner, as described in U.S. Pat. No. 6,007,028. Take cavity 122 as a way of example. It comprises four inner surfaces including first and second surfaces 108, 109, each being trapezoid-like-shaped by way of anisotropic etching known in the art. The four inner surfaces are positioned such that first and second surfaces 108, 109 each are oriented at a precise angle of 54.7° with respect to horizontal plane 125. The high-precision and high-degree of reproducibility of the silicon fabrication techniques render angled-dual-axis confocal scanning endoscope 100 a precise and reliable optical alignment, along with the ease in assembly and mass-production. The fabrication processes of silicon scanning mirrors, such as scanning mirror 104 (or an assembly of two smaller, faster, co-planar scanning mirrors that can be synchronized with closed-loop sensing and control as described above) are also known in the art, as described in U.S. Pat. Nos. 6,007,208, 6,057,952, 5,872,880, 6,044,705, 5,648,618, 5,969,465 and 5,629,790. In most of silicon scanning mirror designs, one or more silicon mirrors and various hinge systems are integrated (e.g., mounted) onto a single silicon substrate. In such a case, silicon substrate 101, dish-cavity 121, and scanning mirror 104. constitute a silicon micro-machined scanning mirror assembly. Moreover, first and second reflective focusing elements 111, 110 can be diffractive optical elements (DOE), reflective diffraction lenses, reflective off-axis binary lenses, curved mirrors, or other reflective focusing means known in the art. Base-plate 103 is typically in the form of a fused silica plate, with a central portion transparent to illumination and observation beams 131, 132 and thereby serving as optical window 123. A separate optical window can also be mounted onto base-plate 103, such that it is disposed between first and second reflective focusing elements 111, 110 for passages of illumination and observation beams 131, 132. First and second reflective focusing elements 111, 110 can be etched into and thereby become an integral part of base-plate 103. (In such a case, there would be no need for pockets 112, 113 shown in FIG. 1A.) Additionally, first and second optical fibers 106, 107 can be single-mode fibers, or multi-mode fibers. First ends 116, 117 of first and second optical fibers 106, 107 are preferably angled-polished, such that their respective end-surfaces are oriented at a predetermined angle (e.g., 15°) with respect the respective fiber axis, as illustrated in FIGS. 1B (or 1D).

It should be noted that in an angled-dual-axis confocal scanning endoscope of the present invention, such as in the embodiment of FIGS. 1A–1B, various constituent elements can be fused into an integral piece, or provided by a single body. Take the embodiment of FIGS. 1A–1B as a way of example. Spacer 102, cavity 122, base-plate 103, first and second reflective focusing elements 111, 110 and optical window 123 can be provided by a molded plastic piece. In such a case, the scanning mirror means, such as scanning mirror 104, can be mechanically coupled to the molded piece by way of a suitable coupling means, such that it is in optical communication with cavity 122.

In an angled-dual-axis confocal scanning system of the present invention, as angled-dual-axis confocal scanning endoscope 100 in FIGS. 1A–1D exemplifies, because the observation beam is positioned at an angle θ relative to the illumination beam (see FIG. 1C), scattered light along the illumination beam does not easily get passed into the observation beam, except where the two beams overlap. This substantially reduces scattered photon noise in the observation beam, thus enhancing the sensitivity and dynamic range of detection. Moreover, by using reflective focusing elements 111, 110 having relatively low numerical aperture (NA) in angled-dual-axis confocal scanning endoscope 100 of the present invention, the illumination and observation beams do not become overlapping until very close to the focus. Such an arrangement prevents scattered light in the illumination beam from directly "jumping" into the corresponding observation beam, hence further filtering out scattered photon. noise in the observation beam. Altogether, the angled-dual-axis confocal scanning endoscope of the present invention has much lower noise and hence yields higher contrast when imaging in a scattering medium, rendering it highly suitable for imaging within biological specimens.

A unique feature of the angled-dual-axis confocal scanning endoscope of the present invention is that the scanning mirror means (such as scanning mirror 104 in FIGS. 1A–1B) is in direct optical communication with the angled-dual-axis focusing means (e.g., an assembly of first and second reflective surfaces 108, 109, and first and second reflective focusing elements 111, 110 in FIGS. 1B or 1D) and the object (e.g., object 130 in FIGS. 1B or 1D) to be examined. This post-objective scanning technique enables the best on-axis illumination and observation point-spread functions to be utilized throughout the entire angular range of an arc-line scan, thereby providing greater resolution over a larger transverse field of view, while maintaining diffraction-limited performance. Such an arrangement is made possible by taking advantage of the longer working distance rendered by using relatively lower NA reflective focusing elements (e.g., first and second reflective focusing elements 111, 110 in the above embodiment) in the angled-dual-illumination-axis means.

As such, angled-dual-axis confocal scanning endoscope of FIGS. 1A–1B provides an exemplary embodiment of a miniaturized, high precision, fast scanning, and low-noise confocal endoscope that advantageously exploits the high-precision and versatility of the silicon fabrication technology, along with the flexibility and scalability rendered by optical fibers. Such an endoscope would be highly desirable in a variety of applications, particular bio-medical applications, for it can be readily implanted inside patients (or animals), providing high resolution and real-time imaging. Those skilled in the art will recognize that the specific arrangements among various optical elements and optical fibers in the above embodiments can be altered in many ways without deviating from the principle and the scope of the present invention. Moreover, there are many other ways to construct a small and integrated angled-dual-axis confocal scanning endoscope in accordance with the present invention.

The embodiment of FIGS. 1A–1B (or FIG. 1D) can be further utilized to perform two-photon (and multi-photon) fluorescence microscopy, so as to exploit its high resolution and low noise capabilities. Whereas traditional single-photon fluorescence laser microscopy requires only a single photon $\lambda_3$ for excitation, two-photon fluorescence microscopy requires simultaneous absorption of two photons $\lambda_1$ and $\lambda_2$ for excitation. In terms of energy, $hc/\lambda_3 = hc/\lambda_1 + hc/\lambda_2$. Thus, $\lambda_1$ and $\lambda_2$ are both longer in wavelength than $\lambda_3$. However, it is important to note that $\lambda_2$ need not necessarily equal $\lambda_1$. Indeed, any combination of wavelengths can be used, so long as the net energy requirements for exciting a particular type of fluorophores are satisfied. Accordingly, two-photon (or multi-photon) fluorescence microscopy has been used in the art for imaging various types of fluorophores (or fluorophore indicators attached to proteins and biological cells) that are of particular interest to biomedical applications.

To create two-photon (and multi-photon) fluorescence, two illumination beams are directed to intersect synergistically in an angled-dual-axis confocal arrangement as shown in the embodiment of FIGS. 1B (or 1D). Accordingly, each of the two observation beams thus produced is in a synergistic confocal arrangement with its corresponding illumination beam, as illustrated in FIG. 1C.

Figure 2A:
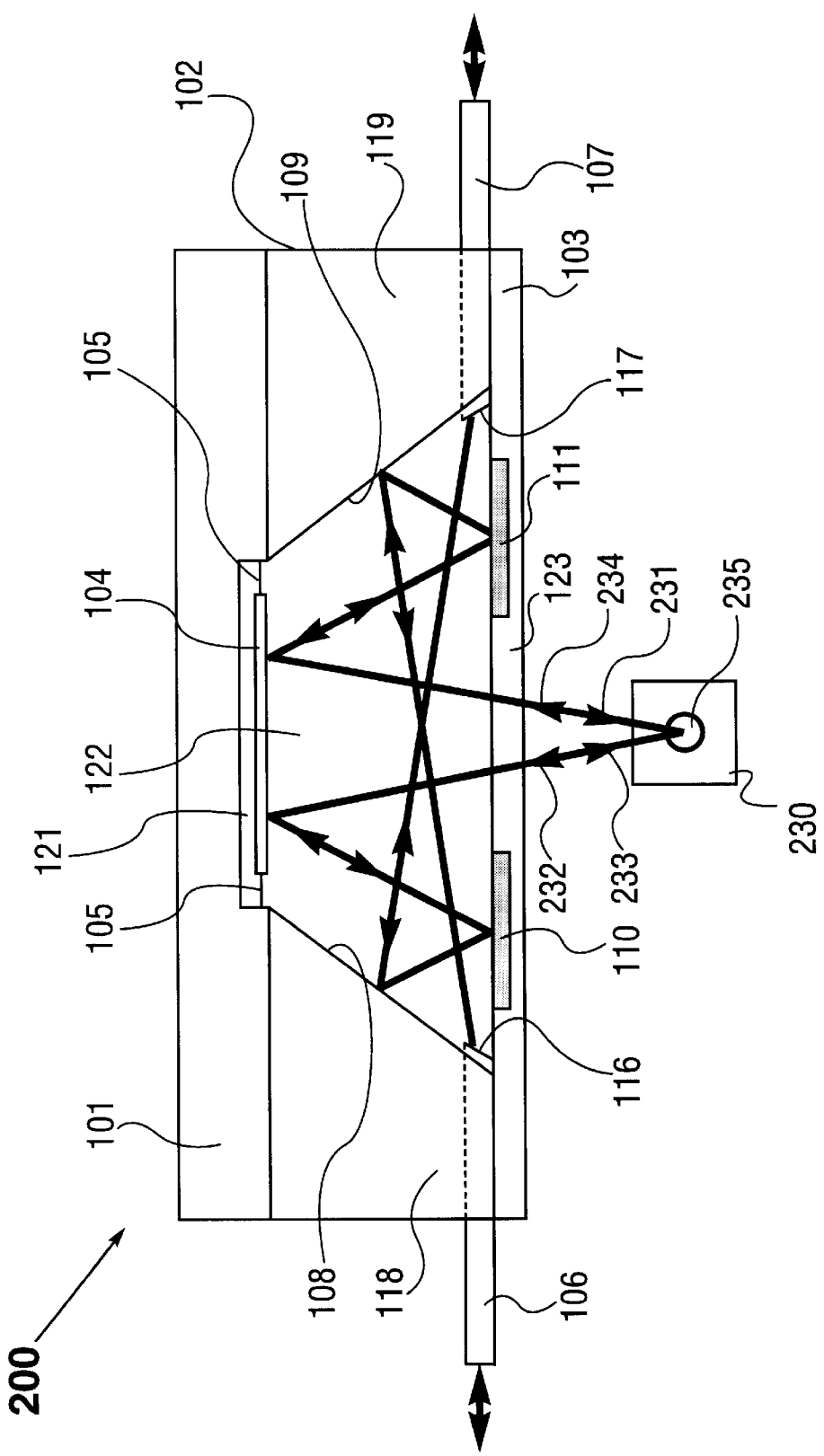
FIGS. 2A–2B depict two exemplary embodiments of a second integrated angled-dual-axis confocal scanning endoscope employing two illumination beams according to the present invention.

FIG. 2A shows a cross-sectional view of an exemplary embodiment of a second angled-dual-axis confocal scanning endoscope employing two illumination beams, according to the present invention. By way of example, angled-dual-axis confocal scanning endoscope 200 makes use of the same embodiment shown in FIGS. 1A–1B, and hence share the same constituent elements as identified by those with the same numbers. A first illumination beam 231 with a first wavelength $\lambda_1$ emerges from first end 116 of first optical fiber 106 and is directed to second reflective surface 109, which in turn deflects the first illumination beam to first reflective focusing element 111. The focused first illumination beam is then passed onto and further directed by scanning mirror 104 through optical window 123 to a first diffraction-limited focal volume (see FIG. 1C) within an object 230. Similarly, a second illumination beam 233 with a second wavelength $\lambda_2$ emerges from first end 117 of second optical fiber 107 and is directed to first reflective surface 108, which in turn deflects the second illumination beam to second reflective focusing element 110. The focused second illumination beam is then passed onto and further directed by scanning mirror 104 through optical window 123 to a second diffraction-limited focal volume (see FIG. 1C) within object 230. Accordingly, a first observation beam 232 emanated from a diffraction-limited confocal overlapping volume 235 within object 230 passes through optical window 123 into cavity 122. First observation beam 232 is then collected by scanning mirror 104, and further deflected to second beam-focusing element 110. The focused first observation beam is then passed onto first reflective surface 108, which in turn directs the beam to first end 117 of second optical fiber 107. Likewise, a second observation beam 234 emanated from confocal overlapping volume 235 passes through optical window 123 into cavity 122. Second observation beam 234 is then collected by scanning mirror 104, and further deflected to first beam-focusing element 111. The focused second observation beam is then passed onto second reflective surface 109, which in turn directs to first end 116 of first optical fiber 106.

It should be emphasized that in the embodiment of FIG. 2A, each of the illumination beams intersects synergistically with its corresponding observation beam as illustrated in FIG. 1C. Moreover, each of the observation beams should be construed in a broad sense as comprising any light transmitted back from the object, including reflected light, scattered light, and fluorescent light. The first and second illumination beams may have the same wavelength, for instance, in the infrared range. The fluorescence light thus produced would include one-color two-photon (1C2P) fluorescence light. And this scenario is not limited only to two-photon excitation; in fact, three-photon or higher order multi-photon excitation can be accordingly created. (For example, there can be three infrared photons whose energy sums to the energy required for a single photon transition). Alternatively, the first and second illumination beams may have very different wavelengths. As a way of example, the first wavelength $\lambda_1$ may be in the infrared range, while the second wavelength $\lambda_2$ lies in the visible range. The fluorescence light thus obtained would include two-color two-photon (2C2P) (and possibly higher order multi-photon) fluorescence light. Moreover, there can be situations where the first illumination beam, having a first wavelength in the infrared range, provides a first observation beam containing reflected light of the same wavelength; while the second illumination beam, having a second wavelength in the visible range, gives rise to single-photon excitation and consequently a second observation beam containing such single-photon fluorescence light. All in all, there can be many combinations of the first and second illumination beams with appropriate wavelengths, such that the observation beams thus produced provide a variety of imaging modes, as later described in FIG. 5. A skilled artisan will know how to selectively make use of a particular type of light collected from the object and filter out spurious background light for a given application.

In the embodiment of FIG. 2A, since each observation beam is positioned at an angle relative to its corresponding illumination beam, scattered (or fluorescent) light along an illumination beam does not easily get passed into its corresponding observation beam, except in the region where the beams overlap. This substantially reduces scattered (or fluorescent) photon noise in the particular observation beam (or beams) being used, thus enhancing the sensitivity and dynamic range of detection. Moreover, by using low NA reflective focusing elements in the embodiment of FIG. 2A, the illumination beams and their corresponding observation beams do not become overlapping until very close to the focus. Such an arrangement further prevents scattered (or fluorescent) light in each illumination beam from directly "jumping" to the corresponding observation beam, hence further filtering out scattered (or fluorescent) photon noise in the observation beam. Altogether, angled-dual-axis confocal endoscope 200 of the present invention is also capable of providing much higher contrast when imaging in a scattering (or fluorescent) medium, rendering it highly suitable for biological applications where reflectance and fluorescence imaging are desired.

Figure 2B:
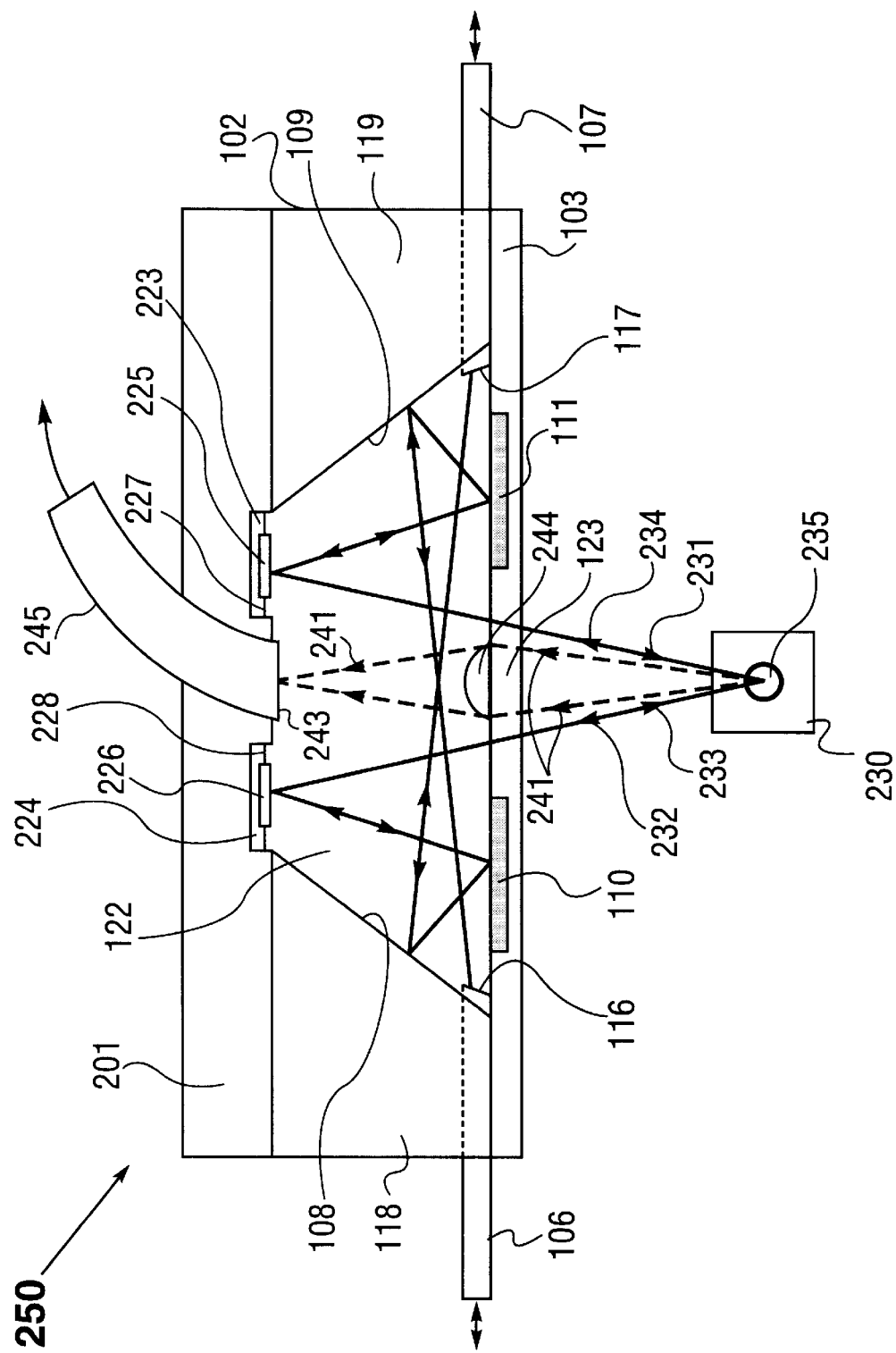

The embodiment of FIG. 2A can be further modified to collect a third observation beam emanated from confocal overlapping volume 235 within object 230. FIG. 2B depicts an exemplary embodiment of a third angled-dual-illumination-axis confocal scanning endoscope of the present invention. As a way of example, angled-dual-axis confocal scanning endoscope 250 is built upon the embodiment of FIG. 2A and hence shares a number of the elements used in the embodiment of FIG. 2A, as indicated by those identified with the same numbers. Silicon substrate 201 in this case contains first and second dish-cavities 223, 224, in which first and second scanning mirrors 225, 226 reside respectively. First and second scanning mirrors 225, 226 are respectively suspended by way of two hinge elements, which also serve as first and second pivoting axes 227, 228 for first and second scanning mirrors 225, 226 respectively. First and second pivoting axes 227, 228 are configured to be substantially co-linear in this exemplary case. Silicon substrate 201 additionally carries a third optical fiber 245, wherein an input end 243 of third optical fiber 245 extends into cavity 122 of silicon spacer 102. A third focusing element 244 is mounted on base-plate 103, such that it is in direct optical communication with optical window 123 of base-plate 103. As in the embodiment of FIG. 2A, first end 116 of first optical fiber 106 extends into cavity 122 by way of first side-wall 118 of silicon spacer 102, such that it is in optical communication with cavity 122. Likewise, first end 117 of first optical fiber 107 extends into cavity 122 by way of second side-wall 119 of silicon spacer 102, so as to be in optical communication with cavity 122.

The overall operation of angled-dual-axis confocal scanning endoscope 250 in the embodiment of FIG. 2B is analogous to that of the embodiment of FIG. 2A as described above. In this case, by rotating about respective pivoting axes 227, 228 in a substantial synchronous and co-rotating manner, first and second scanning mirrors 225, 226 jointly pivot first and second illumination beams 231, 233 (and hence second and first observation beams 234, 232) in such a way that first illumination and observation beams 231, 232, and second illumination and observation beams 233, 234, remain intersecting synergistically at angle θ and that confocal overlapping volume 235 at the intersection of the beams moves along an arc-line within object 130, thereby producing an arc-line scan.

In addition to collecting first and second observation beams 232, 234, a third observation beam 241 emanated from confocal overlapping volume 235 within object 230 is collected by third focusing element 244 through optical window 123. Third focusing element 244 in turn focuses third observation beam 244 to input end 243 of third optical fiber 245. Given that confocal overlapping volume 235 is being scanned under the joint action of first and second scanning mirrors 225, 226, whereas third focusing element 244 along with input end 243 of third optical fiber 245 remain stationary, third optical fiber 245 is preferably a multi-mode fiber of larger diameter (or made of a bundle of multiple optical fibers), so as to maximize the collection efficiency of light emanating from confocal overlapping volume 235 throughout its motion within object 230 during scanning. First and second optical fibers 106, 107 are preferably single-mode fibers. Alternatively, third optical fiber 245 can be replaced by an optical detector mounted onto, or produced as an integral part of silicon substrate 201.

Third observation beam 241 in the embodiment of FIG. 2B comprises predominantly fluorescence light, thereby providing an additional avenue for collecting and detecting fluorescence light of various types (e.g., single-photon fluorescence, one-color two-photon fluorescence, two-color two-photon fluorescence, and multi-photon fluorescence). And additional observation beams of fluorescence can be further collected. The particular way in which third observation beam 241 is collected in the embodiment of FIG. 2B—namely, by stationary third focusing element 244, as opposed to being first collected by either of first and second scanning mirrors 224, 225—is termed a "non-confocal" collection, hereinafter.

In an angled-dual-axis confocal scanning system employing two illumination beams according to the present invention, a third observation beam of predominantly fluorescence light can alternatively (or additionally) be collected by a scanning mirror means, and pivoted concurrently along with the first and second illumination beams (and the corresponding first and second observation beams). As a way of example, this can be accomplished by using an assembly of three scanning mirrors in a predetermined in-line configuration to replace scanning mirror 104 in the embodiment of FIG. 2A, so as to collect first, second and third observation beams. In this arrangement, the two scanning mirrors on the outside are substantially co-planer and synchronized, operating in a way substantially similar to that of first and second scanning mirrors 225, 226 in the embodiment of FIG. 2B. The scanning mirror in the middle is positioned to deflect a third observation beam to a third focusing element mounted onto (or made to be integral to) base-plate 103. The third observation beam is then passed onto a third reflective surface of cavity 122, and subsequently focused into an input end of a third optical fiber. The third optical fiber in this case lies on the same plane as the first and second optical fibers, positioned to be substantially perpendicular to either of first and second optical fibers 106, 107. The first, second and third optical fibers are preferably single-mode fibers in this case. The thus-described way of collecting a third observation beam is termed "confocal-collection", hereinafter. In such a confocal-collection, the point-spread function of the third observation beam is caused to overlap with the confocal overlapping volume of the first and second illumination beams, hence yielding a higher resolution by way of an effective multiplication of the point-spread functions of all three beams. It should be pointed out that although this confocal-collection method may yield high resolution, it is at the expense of a weaker overall optical signal than in the case of the non-confocal collection, as a result of the smaller effective aperture provided by a single-mode fiber. This and other trade-off effects known in the art must be considered when designing a specific device for a given application.

By using the reflective focusing elements with relatively lower NA and allowing for the post-objective scanning, as in the case of FIG. 1B (or FIG. 1D), the embodiments of FIGS. 2A–2B are also able to take advantage of the best on-axis illumination and observation point-spread functions throughout the entire angular range of an arc-line scan, thereby providing greater resolution over a larger transverse field of view, while maintaining diffraction-limited (or relatively aberration-free) performance.

Figure 3A:
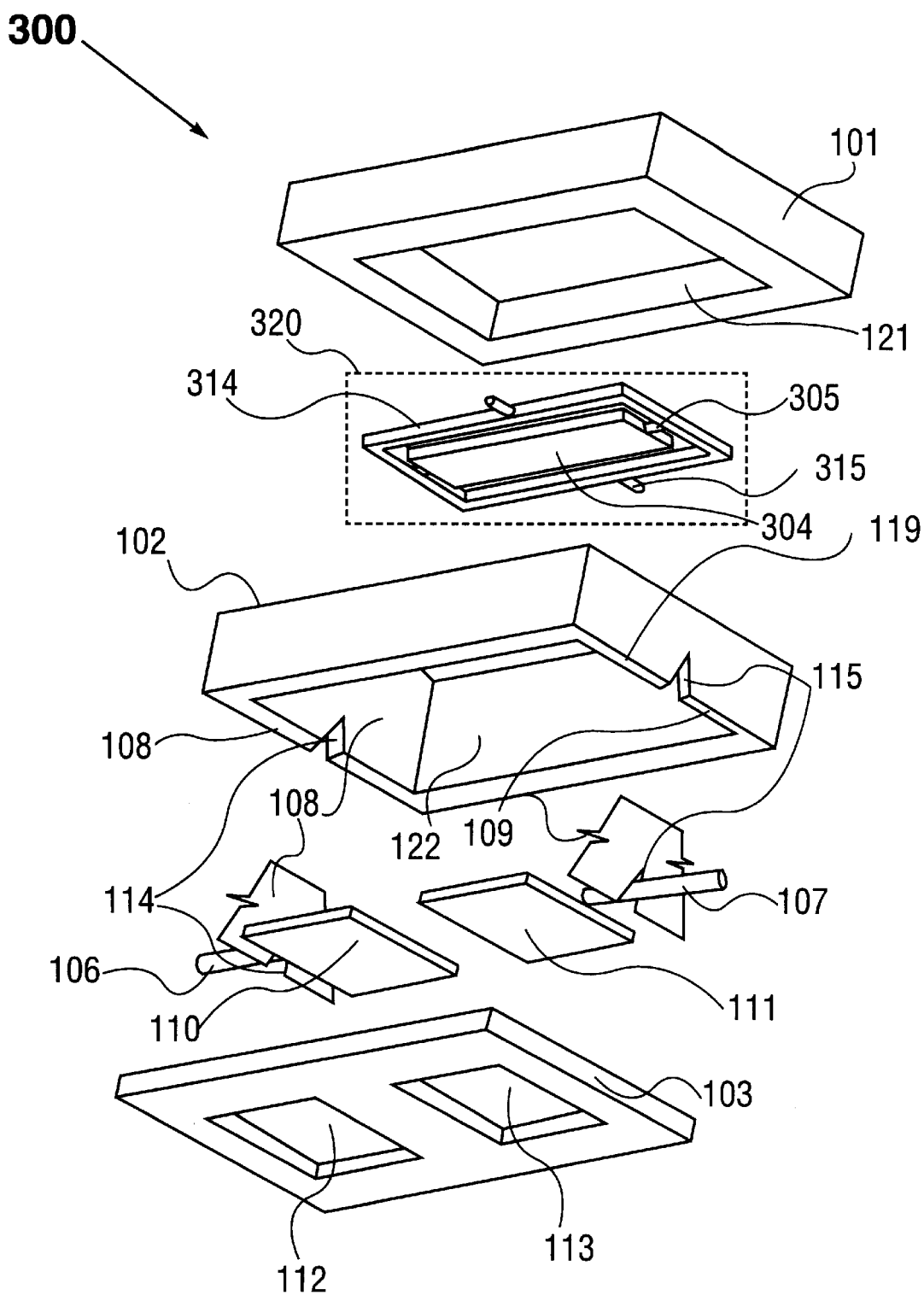
FIGS. 3A–3C show exemplary embodiments of third and fourth integrated angled-dual-axis confocal scanning endoscopes capable of performing multi-axial scanning, according to the present invention.
Figure 3B:
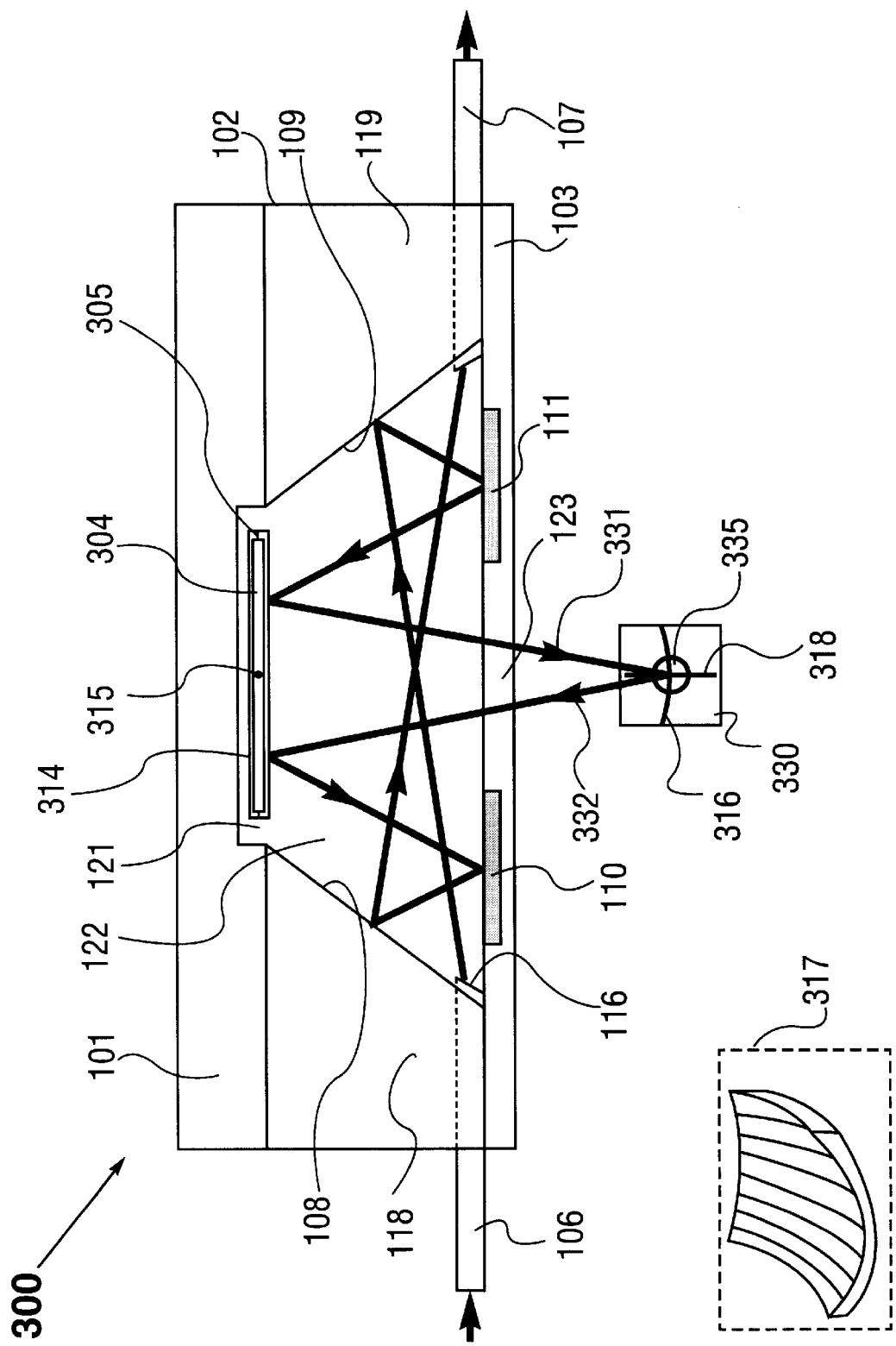
Figure 3C:
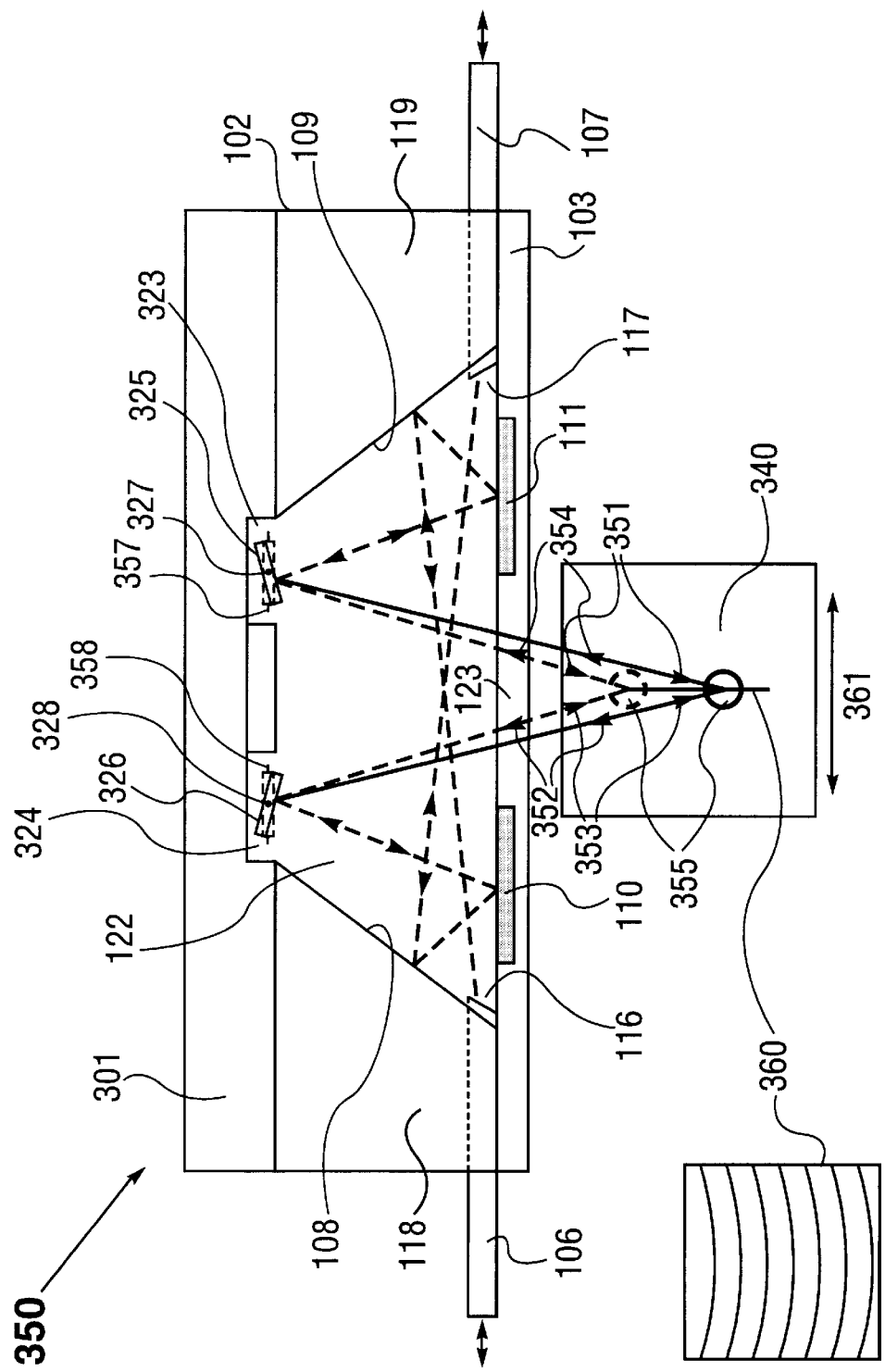

To provide a two-dimensional scan, a scanning mirror means capable of rotating in two orthogonal directions can be implemented in an angled-dual-axis confocal scanning endoscope of the present invention, such as in one of the exemplary embodiments described above. FIGS. 3A–3C show exemplary embodiments of two angled-dual-axis confocal scanning endoscopes according to the present invention. Shown in FIG. 3A is an exploded view of a fourth angled-dual-axis confocal scanning endoscope of the present invention. As a way of example, angled-dual-axis confocal scanning endoscope 300 is constructed in a way similar to the embodiment of FIG. 1A and hence shares some of the elements in FIG. 1A, as indicated by those identified with the same numbers. Substituting single scanning mirror 104 in the embodiment of FIG. 1A is a bi-axial scanning element 320 in the form of a gimbaled assembly of a scanning mirror 304 and a frame 314. Bi-axial scanning element 320 is configured such that scanning mirror 304 can rotate about a first pivoting axis 305, whereas frame 314 along with scanning mirror 304 can rotate about a second pivoting axis 315, thereby providing rotation in two orthogonal directions. (First and second pivoting axes 305, 315 are configured to be substantially orthogonal in this case.)

FIG. 3B shows a cross-sectional view of an assembled version of angled-dual-axis confocal scanning endoscope 300 in FIG. 3A. Scanning mirror 304 along with frame 314 are disposed and suspended in dish-cavity 121 of silicon substrate 101 by way of second pivoting axis 315, which also serves as a hinge means (the specific "hinge mechanism" is not shown in the cross-sectional view of FIG. 3B). Silicon spacer 102 is disposed between silicon substrate 101 and base-plate 103, such that scanning mirror 304 is in direct optical communication with cavity 122 and optical window 123. As in the embodiment of FIG. 1B, first and second reflective focusing elements 111, 110 are mounted in base-plate 103 by way of being situated into first and second pockets 113, 112 (see FIG. 3A) respectively. First optical fiber 106 passes through first side-wall 118 of silicon spacer 102 by way of first V-groove 114 (see in FIG. 3A), such that first end 116 of first optical fiber 106 extends into and thereby is in direct optical communication with cavity 122. Likewise, second optical fiber 107 passes through second side-wall 119 of silicon spacer 102 by way of second V-groove 115 (shown in FIG. 3A), such that first end 117 of second optical fiber 107 extends into and thereby is in direct optical communication with cavity 122. A central portion of base-plate 103 serves as optical window 123 for passages of optical beams.

FIG. 3B further provides an operational view of angled-dual-axis confocal scanning endoscope 300 utilizing one illumination beam. An illumination beam 331 emerges from first end 116 of first optical fiber 106 and is directed to second reflective surface 109, which in turn deflects the illumination beam to first reflective focusing element 111. The focused illumination beam is then passed onto and further directed by scanning mirror 104 through optical window 123 to a first diffraction-limited focal volume (see FIG. 1C) within an object 330. Accordingly, an observation beam 332 emanated from a confocal overlapping volume 335 within object 330 passes through optical window 123 into cavity 122. Observation beam 332 is then collected by scanning mirror 304, and further deflected to second reflective focusing element 110. The focused observation beam is subsequently passed onto first reflective surface 108, which in turn directs the observation beam to first end 117 of second optical fiber 107.

In the embodiment of FIG. 3B, by rotating about first pivoting axis 305, scanning mirror 304 pivots illumination beam 331 and observation beam 332 in such a way that illumination beam 331 and observation beam 332 remain intersecting synergistically and that confocal overlapping volume 335 at the intersection of the two beams moves along an arc-line within object 130, thereby producing an arc-line scan. Moreover, by rotating about second pivoting axis 315 along with frame 314, scanning mirror 304 further causes confocal overlapping volume 335 to move in a predetermined pattern along an arc-cross-sectional surface 316, thereby providing an arc-cross-sectional-surface scan. As a way of example, by rotating scanning mirror 304 about first and second pivoting axes 305, 315 (which provide fast-scanning-axis and slow-scanning-axis respectively, for instance) in a raster-scanning fashion, a successive sequence of arc-line scans can be produced, as illustrated in dashed box 317. Additionally, by translating angled-dual-axis confocal scanning endoscopes 300 along a vertical direction 318 in a incremental way, a successive sequence of arc-cross-sectional-surface scans can be produced, thereby providing a three-dimensional volume scan of object 330.

It should be noted that the embodiment of FIG. 3B can also utilize two illumination beams in a way analogous to the arrangement and operation of the embodiment of FIG. 2A, so as to make use of both reflected and fluorescence light described above.

FIG. 3C depicts an exemplary embodiment of a fourth angled-dual-axis confocal scanning endoscope of the present invention. By way of example, angled-dual-axis confocal scanning endoscope 350 is built upon and hence shares a number of the elements used in the embodiment of FIG. 3B, as indicated by those identified with the same numbers. Silicon substrate 301 in this case contains first and second dish-cavities 323, 324, in which first and second bi-axial scanning elements 325, 326 reside respectively. As a way of example, each of bi-axial scanning elements 325, 326 can be in the form of bi-axial scanning element 320 in the embodiment of FIG. 3B—namely, comprising a gimbaled assembly of a scanning mirror and a frame whereby the scanning mirror can rotate in two orthogonal directions. Other types of scanning means capable of rotating in two orthogonal directions can be alternatively implemented. First and second bi-axial scanning elements 325, 326 are respectively suspended in first and second dish-cavities 323, 324 by way of two hinge elements (the specific "hinge mechanisms" are not shown in the cross-sectional view of FIG. 3C), which also serve as second and fourth pivoting axes 327, 328 for first and second bi-axial-scanning elements 325, 326 respectively. First and second bi-axial-scanning elements 325, 326 can further rotate about first and third pivoting axes 357, 358 respectively. Note that in this exemplary case, first and third pivoting axes 357, 358 are configured to be substantially co-linear, providing a substantially common pivoting axis about which first and second bi-axial-scanning elements 325, 326 can co-rotate. Second and fourth pivoting axes 327, 328 are configured to be substantially parallel and spaced apart, each being orthogonal to either of first and third pivoting axes 357, 358. As such, first and second bi-axial-scanning elements 325, 326 can be made to counter-rotate relative to each other about second and fourth pivoting axes 327, 328 respectively, as illustrated in FIG. 3C. As a way of example to illustrate such a counter-rotating scan, initial positions of first and second bi-axial scanning elements 325, 326 and the corresponding passages of illumination and observation beams 351, 353, 352, 354 are shown by dashed lines; and subsequent positions of counter-rotating first and second bi-axial scanning elements 325, 326 along with the corresponding passages of illumination and observation beams 351, 353, 352, 354 are marked by solid lines in FIG. 3C.

In operation, a first illumination beam 351 with a first wavelength $\lambda_1$ emerges from first end 116 of first optical fiber 106 and is directed to second reflective surface 109, which in turn deflects the first illumination beam to first reflective focusing element 111. The focused first illumination beam is then passed onto and further directed by first bi-axial-scanning element 325 through optical window 123 to a first diffraction-limited focal volume (see FIG. 1C) within an object 340. Similarly, a second illumination beam 353 with a second wavelength $\lambda_2$ emerges from first end 117 of second optical fiber 107 and is directed to first reflective surface 108, which in turn deflects the second illumination beam to second reflective focusing element 110. The focused second illumination beam is then passed onto and further directed by second bi-axial-scanning element 326 to a second diffraction-limited focal volume (see FIG. 1C) within object 340. Accordingly, a first observation beam 352 emanated from a diffraction-limited confocal overlapping volume 355 within object 340 passes through optical window 123 into cavity 122. First observation beam 352 is then collected by second bi-axial scanning element 326, and further deflected to second reflective focusing element 110. The focused first observation beam is subsequently passed onto first reflective surface 108, which in turn directs the beam to first end 117 of second optical fiber 107. Likewise, a second observation beam 354 emanated from confocal overlapping volume 355 passes through optical window 123 into cavity 122. Second observation beam 354 is then collected by first bi-axial scanning element 325, and further deflected to first beam-focusing element 111. The focused second observation beam is subsequently passed onto second reflective surface 109, which in turn directs the beam to first end 116 of first optical fiber 106.

In the above embodiment, by rotating about first and third pivoting axes 357, 358 in a substantially synchronous and co-rotating manner, first and second bi-axial-scanning elements 325, 326 jointly pivot first and second illumination beams 351, 353 (and hence second and first observation beams 354, 352) in such a way that first illumination and observation beams 351, 352, and second illumination and observation beams 353, 354, remain intersecting synergistically and that confocal overlapping volume 355 at the intersection of the beams moves along an arc-line within object 340, thereby producing an arc-line scan. Moreover, by counter-rotating about second and fourth pivoting axes 327, 328 respectively, first and second bi-axial scanning element 325, 326 further cause confocal overlapping volume 355 to move in a predetermined pattern along a vertical-cross-section plane 360, thereby providing a vertical-cross-sectional scan. For instance, by first co-rotating and then counter-rotating first and second bi-axial scanning element 325, 326 in a raster-scanning fashion (co-rotating motion provides fast scanning and counter-rotating provides slow scanning in this case), a successive sequence of arc-line scans that progressively deepen into the interior of object 340 along vertical-cross-section plane 360 can be produced, as illustrated in FIG. 3C. Alternatively, by first counter-rotating and then co-rotating first and second bi-axial scanning elements 325, 326 in a raster-scanning fashion (counter-rotating motion provides fast scanning and co-rotating provides slow scanning in this case), a sequence of "radial-line" scans that are angularly spaced apart in a fan-like pattern along vertical-cross-sectional plane 360 within object 340 can be produced. (Note: the "radial-line" scans in this case are so termed because they are not parallel to each other: that is, they can be viewed as "radiating " out from the center of curvature of an arc-line located within vertical-cross-section plane 360.) For this alternative raster-scanning pattern, it is preferable to reconfigure bi-axial scanning elements 325, 326 in such a way that first pivoting axis 357 and second pivoting axis 327 are switched in relation to that shown in FIG. 3C, and likewise for third pivoting axis 358 and fourth pivoting axis 328. This configuration further permits the bi-axial scanning elements to be hinged to a single common frame that can rotate about a common pivoting axis, which provides the slower arc-scanning action. Additionally, by translating angled-dual-axis confocal scanning endoscope 350 in a transverse direction 361 perpendicular to vertical-cross-section plane 360 in an incremental manner, a three-dimensional volume scan of object 340 can be produced.

In applications where vertical-line scans are desired, two uni-axial scanning mirrors, such as two uni-axial silicon micro-machined scanning mirrors, can be used to replace first and second bi-axial scanning element 325, 326 in the embodiment of FIG. 3C. In this case, each of the two scanning mirrors can be made to rotate about an individual pivoting axis, where the two individual pivoting axes are substantially parallel and spaced apart, configured in a way substantially similar to second and fourth pivoting axes 327, 328 in the embodiment of FIG. 3C. By counter-rotating relative to each other about these two pivoting axes respectively, the two scanning mirrors can cause confocal overlapping volume 355 to progressively deepen into the interior of object 340 along a vertical line (located within vertical-cross-sectional plane 360), thereby producing a vertical-line scan.

In the embodiment of FIG. 3C, a third observation beam comprising predominantly fluorescence light can be further collected, in a manner similar to the arrangement and operation of the embodiment of FIG. 2B (or other embodiments described above). The embodiment of FIG. 3C may alternatively utilize a single illumination beam in a way analogous to the operation of the embodiment of FIG. 3B.

Figure 4:
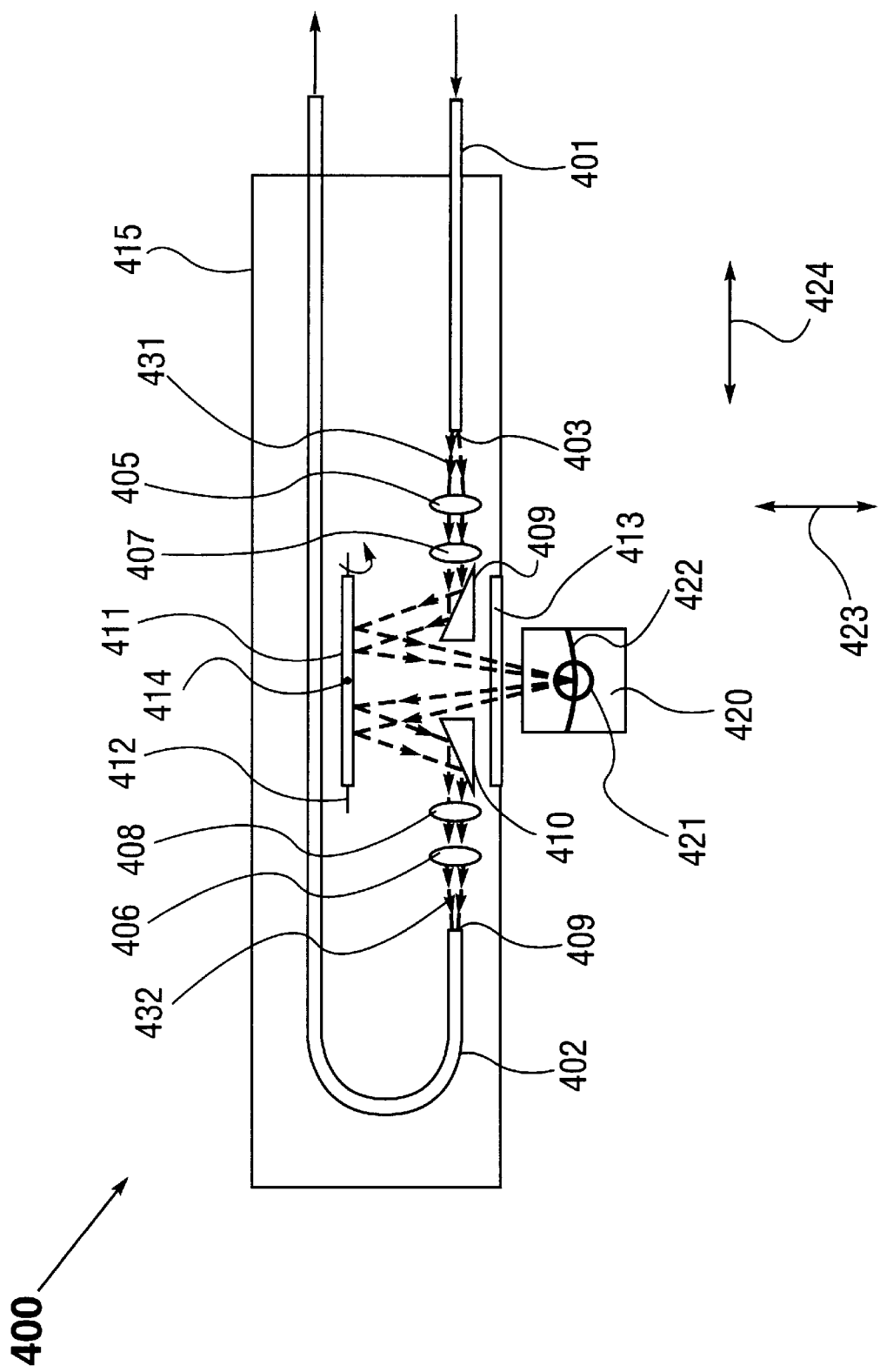
FIG. 4 shows an alternative embodiment of an angled-dual-axis confocal scanning endoscope of the present invention.

FIG. 4 illustrates an alternative way of constructing an angled-dual-axis confocal scanning endoscope according to the present invention, where silicon fabrication technology need not be utilized. Angled-dual-axis confocal scanning endoscope 400 comprises first and second optical fibers 401, 402; first and second beam-collimating elements 405, 406; first and second beam-focusing elements 407, 408; first and second reflective elements 409, 410; a scanning mirror means in the form of a bi-axial scanning element 411; and an optical window 413 mounted on a cylindrical case 415, which encloses the entire assembly thus described. Bi-axial scanning element 411 in this case can rotate about first and second pivoting-axes 412, 414, which are substantially orthogonal to each other.

In operation, an illumination beam 431 emitted from a first end 403 of first optical fiber 401 is first collimated by first beam-collimating element 405 and subsequently focused by first beam-focusing element 407. The focused illumination beam is then passed onto first reflective element 409, and further deflected to bi-axial scanning element 411, which in turn directs the illumination beam through optical window 413 to a first focal volume (see FIG. 1C) within an object 420. An observation beam 432 emanated from a confocal overlapping volume 421 within object 420 passes through optical window 413 and is then collected by bi-axial scanning element 411. Observation beam 432 is subsequently directed to second reflective element 410, which in turn passes the observation beam to second beam-focusing element 408. The collimated observation beam is further passed onto second beam-collimating element 406, which in turn focuses the beam to a first end 409 of second optical fiber 402. By rotating about first pivoting axis 412, bi-axial scanning element 411 pivots illumination and observation beams 431, 432 in such a way that illumination beam 431 and observation beam 432 remain intersecting synergistically and that confocal overlapping volume 421 at the intersection of the two beams moves along an arc-line within object 420, thereby producing an arc-line scan. Moreover, by rotating about second pivoting axis (slow-scanning-axis) 414, bi-axial scanning element 411 further causes confocal overlapping volume 421 to move successively in a sequence of arc-line scans along an arc-cross-sectional-surface 422 within object 420, thereby providing an arc-cross-sectional-surface scan (similar to what is shown in dashed box 317 in FIG. 3B). Additionally, by translating angled-dual-axis confocal scanning endoscope 400 along a vertical direction 423 in an incremental way, a successive sequence of arc-cross-sectional-surface scans that progressively deepen into the interior of object 420 can be produced, which can be assembled to provide a three-dimensional volume image of object 420.

Alternatively in the aforementioned embodiment, by rotating bi-axial scanning element 411 first about second pivoting axis (fast-scanning-axis) 414 and then about first pivoting axis (slow-scanning-axis) 412 in a raster-scanning manner, a sequence of arc-line scans along an arc-cross-sectional-surface 422 as described above can be produced, thereby providing an arc-cross-sectional-surface scan. Moreover, by translating angled-dual-axis confocal scanning endoscope 400 along a vertical direction 423 in an incremental way, a successive sequence of arc-cross-sectional-surface scans in vertical direction 423 can be produced, which can be assembled to provide a three-dimensional volume image of object 420.

In general, the scanning mirror means in the embodiment of FIG. 4 can be a uni-axial or bi-axial scanning mirror, an assembly of two smaller (and therefore faster) scanning mirrors wherein each can rotate in one or two directions, a gimbaled assembly of a scanning mirror and a frame (as shown in FIGS. 3A–3B), a combination of two such gimbaled assemblies (as shown in FIG. 3C), or any other uni-axial or bi-axial scanning means known in the art. Other scanning modes can also be utilized for particular applications. For instance, a scanning mirror means operationally equivalent to that described in FIG. 3C can be used, thereby producing a vertical-cross-sectional scan. Additionally, angled-dual-axis confocal scanning endoscope 400 can be translated along horizontal direction 424 in FIG. 4 to produce a three-dimensional volume scan. First and second beam-collimating elements 405, 406 can be collimating lenses. First and second beam-focusing elements 407, 408 can be focusing lenses. Each of first and second reflective elements 409, 410 may be in the form of a flat (or curved) mirror. Angled-dual-axis confocal scanning endoscope 400 in the embodiment of FIG. 4 can be packaged into a stainless steel tube housing (such as cylindrical case 415) having diameter of 1–5 mm for insertion into arteries, so as to image the inner walls of the arteries by utilizing an appropriate scanning mode of the scanning mirror means. As a way of example, a vertical-line scan can be provided by a scanning mirror means comprising two uni-axial counter-rotating scanning mirrors. This vertical-line scan can then be swept through a cross-section of an artery by rotating the endoscope about the cylindrical axis of the tubular housing, thereby generating a fan-like scan pattern.

It should be noted that various elements and their configuration in the embodiment of FIG. 4 can be altered in many ways without deviating from the principle and scope of the present invention. Two illumination beams can also be employed in angled-dual-axis confocal scanning endoscope 400 of FIG. 4, so as to provide an assortment of reflectance and fluorescence images. An advantage of angled-dual-axis confocal scanning endoscope 400 as illustrated in FIG. 4 is that it can be configured and assembled in a customer-tailored way so to accommodate a practical application. Those skilled in the art will know how to design an angled-dual-axis confocal scanning endoscope according to the present invention for a given application.

As such, the present invention provides a novel class of angled-dual-axis confocal scanning endoscopes that are highly integrated and scalable, thereby allowing for miniaturization. Such integrated angled-dual-axis confocal scanning endoscopes, as the above exemplary embodiments demonstrate, are capable of providing various line and cross-sectional-surface scans with enhanced resolution, faster speed, and higher sensitivity. Moreover, by employing two illumination beams in an angled-dual-axis confocal scanning endoscope of the present invention, two-photon (and multi-photon) fluorescence light can be produced and detected along with reflected light, thereby providing an assortment of reflectance and fluorescence images, as described below.

Figure 5:
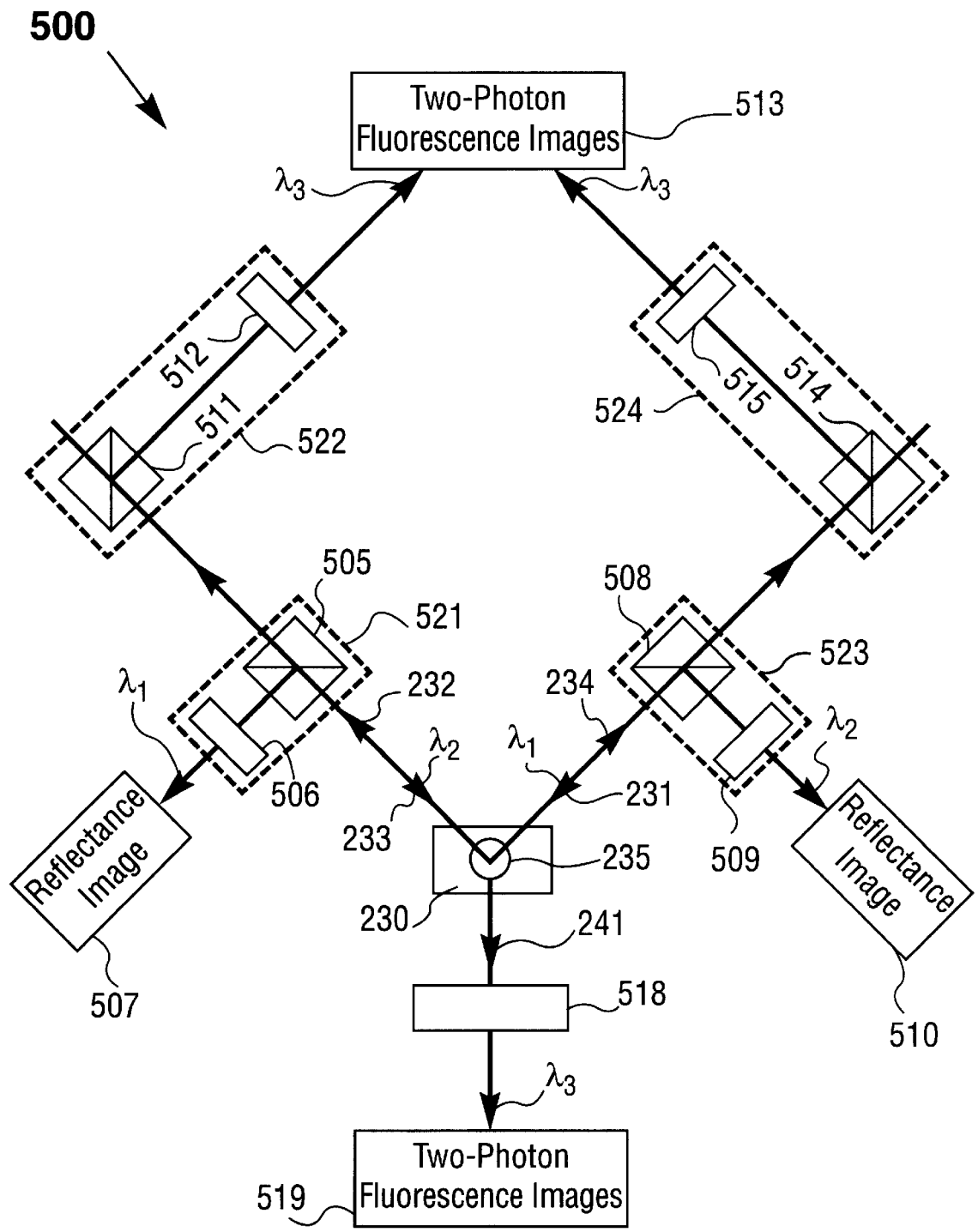
FIG. 5 provides a schematic depiction of how to make use of various optical beams collected by an angled-dual-axis confocal scanning endoscope employing two illumination beams, according to the present invention.

FIG. 5 provides a schematic illustration of how to make use of the multiple beams collected from an object by an angled-dual-axis confocal scanning endoscope employing two illumination beams, according to the present invention. In schematic illustration 500, first illumination beam 231 with a first wavelength $\lambda_1$ and second illumination beam 233 with a second wavelength $\lambda_2$ are directed to intersect at a confocal overlapping volume 235 within an object 230. Accordingly, first and second observation beams 232, 234 emanated from confocal overlapping volume 235 are transmitted back along the reverse directions of second and first illumination beams 232, 231 respectively. To make use of the collected observation beams, a first beam-splitter 505 is optically coupled to first observation beam 232, serving to route a portion of first observation beam 232 to a first optical filter 506. First optical filter 506 may be configured such that only the reflected light with wavelength $\lambda_1$ carried by first observation beam 232 is permitted to pass though, thereby providing a first reflectance image 507. A second beam-splitter 511 can be further coupled to first observation beam 232, so as to route an additional amount of first observation beam 232 to a second optical filter 512. Second optical filter 512 may be designed such that only the two-photon fluorescence light with a third wavelength $\lambda_3$ ($1/\lambda_3=1/\lambda_1+1/\lambda_2$) carried by first observation beam 232 is permitted to pass though, thereby providing a two-photon fluorescence image 513. Likewise, a third beam-splitter 508 is optically coupled to second observation beam 234, serving to route a fraction of second observation beam 234 to a third optical filter 509. Third optical filter 509 may be configured to permit only the reflected light with wavelength $\lambda_2$ carried by second illumination beam 234 to pass though, thereby providing a second reflectance image 510. A fourth beam-splitter 514 can be further coupled to second observation beam 234, serving to route an additional amount of second observation beam 234 to a fourth optical filter 515. Fourth optical filter 515 can be designed to permit only the two-photon fluorescence light with wavelength $\lambda_3$ carried by second observation beam 234 to pass though, thereby further contributing to two-photon fluorescence image 513. Additionally, a third observation beam 241 emanated from confocal overlapping volume 235 can be collected and routed to a fifth filter 518, which preferentially allows only the two-photon fluorescence light with wavelength $\lambda_3$ to pass through, thereby producing an additional two-photon fluorescence image 519. (The two-photon fluorescence light provided by the third observation beam may also be combined with the two-photon fluorescence light extracted from the first and second observation beams to create a combined two-photon fluorescence image.)

As the embodiment of FIG. 5 demonstrates, a cascade of the beam-splitter/filter elements (or other types of wavelength-selective beam-splitting means) can be optically coupled to either of the first and second observation beams, enabling various spectral components of each of the observation beams to be extracted and detected. Note that various assemblies of beam-splitting and beam-filtering elements in the embodiment of FIG. 5, as outlined by dashed boxes 521, 522, 523, 524, effective constitute wavelength-selective-beam-splitting elements and hence can be replaced by other types of wavelength-selective-beam-splitting means known in the art. As such, by using one or more of the three available observation beams, with the proper wavelengths selected for the first and second illumination beams, and proper wavelength-selective-beam-splitting means for spectral extraction and detection, an angled-dual-illumination-axis confocal scanning endoscope of the present invention is capable of providing an assortment of reflectance images, single-photon fluorescence images, one-color two-photon (1C2P) fluorescence images, two-color two-photon (2C2P) fluorescence images, and multi-photon fluorescence images. Furthermore, a superposition of reflectance images and two-photon fluorescence images can be particularly powerful in characterizing a biological sample, for the two types of the images reveals complimentary characteristics of the sample. That is owing to the fact that the reflectance image is generally effective in mapping out the morphology of the sample (such as a particular arrangement or pattern of cells), whereas the two-photon fluorescence image is unique in mapping out particular types of fluorophores contained in the sample (which can reveal the functionality of the cells). Those skilled in the art can selectively make use of the imaging capabilities provided by an angled-dual-axis confocal scanning endoscope of the present invention, so as to best suit a given application.

It should also be noted that while it is possible to operate the present invention in a number of ways that may provide different combinations of reflectance and fluorescence images (such as single-photon, two-photon, or multiple-photon images), depending upon the instrument design and the types of light sources/wavelengths used, it is preferable to design the instrument in a way that maximizes the resolution of the images thus produced and contemporaneously minimizes the scattered and/or fluorescent photon noise in the image signals. This can be best accomplished by the following seven design rules, which insure that scattered or fluorescence light generated by each illumination beam is mostly collected only by its corresponding (angularly overlapping) observation beam:

(1) In the case where the first observation beam is being used to collect reflectance image information characterized by a first wavelength, the second illumination beam should not include light with the first wavelength, and the first illumination beam must provide light with the first wavelength.

(2) In the case where the first observation beam is being used to collect single-photon fluorescence image information characterized by a third wavelength when the object is excited by light of a second wavelength, the second illumination beam should not include single-photon excitation light with the second wavelength, and the first illumination beam should provide single-photon excitation light with the second wavelength.

(3) In the case where the first observation beam is being used to collect one-color two-photon (1C2P) fluorescence image information characterized by a fifth wavelength when the object is excited by light of a fourth wavelength, the second illumination beam should not include 1C2P excitation light with the fourth wavelength, and the first illumination beam should provide 1C2P excitation light with the fourth wavelength.

(4) In the case where either of the first and second observation beams, or both of the observation beams, are being used to collect two-color two-photon (2C2P) fluorescence image information characterized by an eighth wavelength when the object is excited by light that requires both of sixth and seventh wavelengths, the first and second illumination beams should each provide light with only one of the two required wavelengths, such that 2C2P excitation light is provided only in the region where the two illumination beams overlap both spatially and temporally.

(5) In the case where the second observation beam is being used to collect reflectance image information characterized by a ninth wavelength, the first illumination beam should not include light with the ninth wavelength, and the second illumination beam must provide light with the ninth wavelength.

(6) In the case where the second observation beam is being used to collect single-photon fluorescence image information characterized by an eleventh wavelength when the object is excited by light of a tenth wavelength, the first illumination beam should not include single-photon excitation light with the tenth wavelength, and the second illumination beam should provide single-photon excitation light with the tenth wavelength.

(7) In the case where the second observation beam is being used to collect one-color two-photon (1C2P) fluorescence image information characterized by a thirteenth wavelength when the object is excited by light of a twelfth wavelength, the first illumination beam should not include 1C2P excitation light with the twelfth wavelength, and the second illumination beam should provide 1C2P excitation light with the twelfth wavelength.

Figure 6:
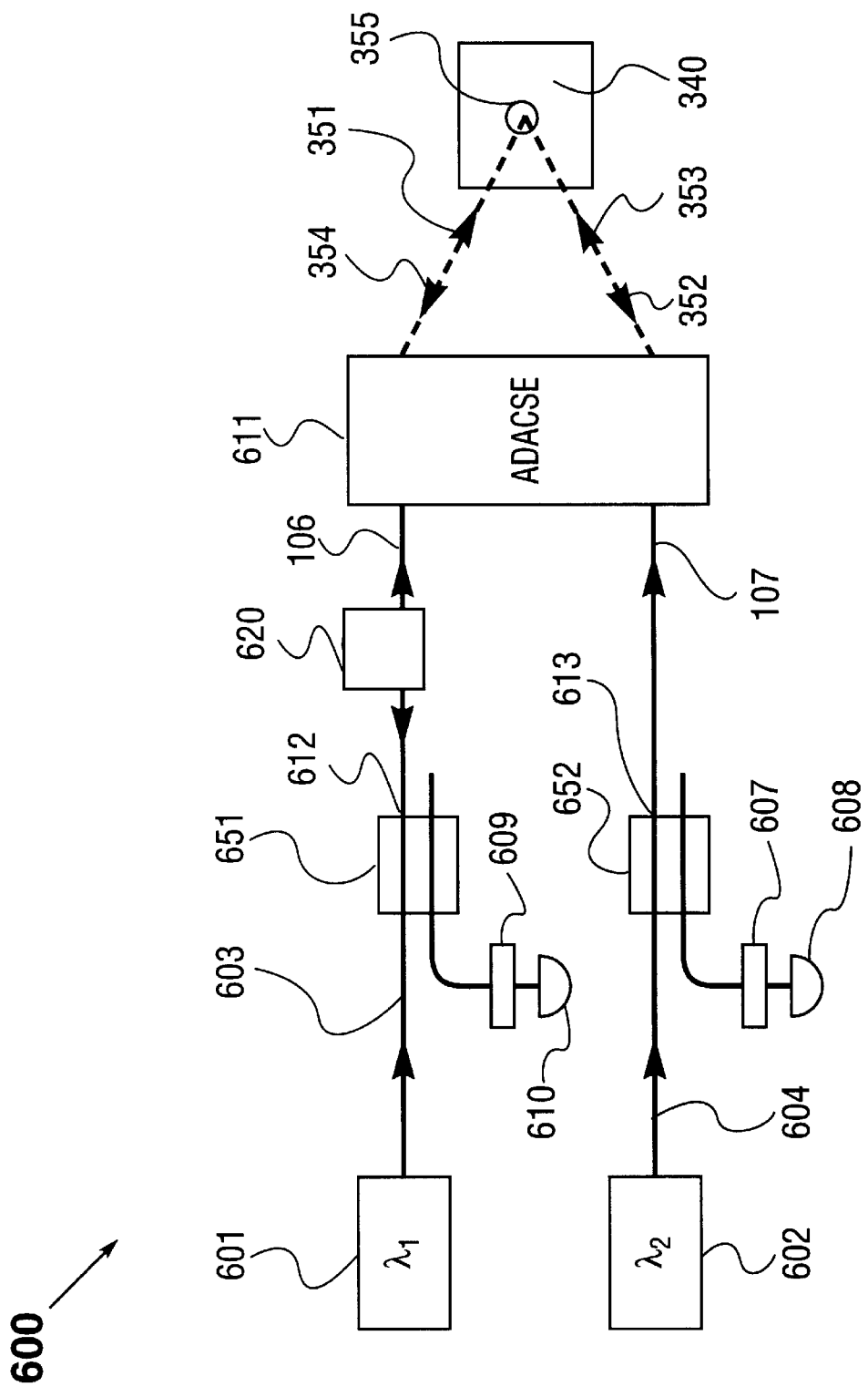
FIG. 6 shows a simplified schematic diagram of an exemplary angled-dual-axis confocal scanning system according to the present invention.

FIG. 6 depicts an exemplary embodiment of an angled-dual-axis confocal scanning system of the present invention, providing an exemplary illustration of how an angled-dual-axis confocal scanning endoscope of the present invention can be implemented in a practical application, so as to utilize various imaging capabilities discussed in FIG. 5. Angled-dual-axis confocal scanning system 600 comprises an angled-dual-axis confocal scanning endoscope (ADACSE) 611, first and second light sources 601, 602, first and second optical fibers 106, 107, third and fourth optical fibers 603, 604, first and second fiber-optic couplers 651, 652, and an optical delay device 620. By way of example, angled-dualaxis confocal scanning endosocpe 611 is in a simplified schematic form of the embodiment shown in FIG. 3C. Any other embodiment in accordance with the present invention can be alternatively implemented.

In angled-dual-axis confocal scanning system 600, first light source 601 is optically coupled to first fiber-optic coupler 651 by way of third optical fiber 603. First fiber-optic coupler 651 is in turn coupled to second end 612 of first optical fiber 106, such that first illumination beam 351 is transmitted to angled-dual-axis confocal scanning endoscope 611. Similarly, second light source 602 is optically coupled to second fiber-optic coupler 652 by way of fourth optical fiber 604. Second fiber-optic coupler 652 is in turn coupled to second end 613 of second optical fiber 107, such that second illumination beam 353 is transmitted to angled-dual-axis confocal scanning microscope 611. In this case, first observation beam 352 collected by angled-dual-axis confocal scanning endoscope 611 is delivered back to second fiber-optic coupler 652 by second optical fiber 107, where a fraction of first observation beam 352 is diverted to first optical detector 608 via first optical filter 607. As such, a desirable spectral component (e.g., reflected light, or two-photon fluorescence light) carried by first observation beam 352 can be extracted and detected. Likewise, second observation beam 354 collected by angled-dual-axis confocal scanning endoscope 611 is delivered back to first fiber-optic coupler 651 by first optical fiber 106, where a fraction of second observation beam 354 is diverted to second optical detector 610 via second optical filter 609. As such, a desirable spectral component (e.g., reflected light, or two-photon fluorescence light) carried by second observation beam 354 can be extracted and detected. In case where first and second light sources 601, 602 are pulsed lasers, such as sub-picosecond pulsed lasers, adjustable optical delay device 620 serves to ensure a concurrent spatial and temporal overlap of first and second illumination beams 351, 353. As a way of example, each of first and second fiber-optic couplers 651, 652 can be a 50/50 fiber-optical coupler. For a better efficiency, each of first and second fiber-optic couplers 651, 652 can also be a fiber-optic wavelength division multiplexer (WDM) of a proper design, which is known in the art of broadband fiber-optic communications systems.

In the angled-dual-axis confocal scanning system described above, fiber-optic couplers are used to serve as beam-splitting means. Optical fibers, preferably single-mode fibers, are employed for the purpose of providing optical coupling. Alternatively, the combined function of a fiber-optic coupler and the corresponding optical filter (such as fiber-optic coupler 651 and optical filter 609, or fiber-optic coupler 652 and optical filter 607), effectively serving as a wavelength-selective-beam-splitting means, can be replaced by a functionally equivalent and nonetheless more efficient fiber-optic wavelength division mutiplexer (WDM). These fiber-optic components, along with the fiber-coupled angled-dual-axis confocal scanning endoscope of the present invention, enables the confocal scanning system thus constructed to be all fiber-based systems, hence fully exploiting the flexibility, scalability, ruggedness and economical value afforded by optical fibers.

Alternatively, those skilled in the art may substitute the fiber-optic couplers and WDM's by other types of wavelength-selective-beam-splitting and beam-routing means such as assemblies of dichroic beam-splitters and dichroic filters, and replace the optical fibers by other types of free space or bulk optical coupling means well known in the art, in the angled-dual-illumination-axis confocal scanning systems of the present invention, without deviating from the principle and the scope of the present invention. Further, the methods for detection of optical signals and for electronic processing of the detected optical signals into images are well known in the art. A skilled artisan can make suitable design choices for a given application.

All in all, the angled-dual-axis confocal scanning endoscope of the present invention provides many advantages over the prior art confocal systems, most notably: enhanced axial resolution while maintaining a workable working distance and a large field of view, fast and high-precision scanning, lower noise and larger dynamic range of detection, and a highly integrated and scalable structure. Such an angled-dual-axis confocal scanning endoscope can be readily miniaturized, rendering it highly desirable for in-vivo imaging of biological specimens. Moreover, by employing two illumination beams, an angled-dual-axis confocal scanning endooscope of the present invention is capable of providing an assortment of reflectance and fluorescence images, rendering it particularly powerful for imaging biological samples. Additionally, the integration of the angled-dual-axis confocal scanning endoscope of the present invention with fiber-optic components and fiber-coupled laser sources provides an assembly of fiber-based angled-dual-axis confocal scanning systems, which are specially useful tools for biological and medical imaging applications, such as instruments for performing in vivo optical biopsies. For example, a miniaturized angled-dual-axis confocal scanning endoscope of the present invention can be used as a catheter that is placed within very small cavities of a living body for disease detection. In some applications, it may also be implanted within such cavities for continuous monitoring of biological functions at a cellular level.

For biological tissue imaging applications, the useful wavelengths of light generally ranges from about 0.4 microns to 1.6 microns. Embodiments of the angled-dual-illumination-axis confocal scanning microscope of the present invention are capable of achieving resolutions of about 1–5 microns in the axial as well as the transverse directions, by use of illumination and observation lenses with NA typically ranging from 0.1 to 0.4, and the intersecting angle θ typically ranging from 45° to 90°. A typical vertical cross-section scan area may be on the order of about 0.1–1 millimeter in both directions. In terms of scanning capabilities, the fast scan rate along an arc-line typically ranges from 1 to 10 kHz, and the maximum rotation angle from a neutral position of the scanning mirror (e.g., scanning mirror 104 in FIG. 1B) may range from one to several degrees. Generally, the smaller and the lighter the scanning mirror, the faster the scanning rate. For instance, using a silicon micro-machined scanning mirror can provide scanning rates approaching 10 kHz. Two-dimensional raster scanning can be performed by providing a slow-scanning-axis at a rate of about 1–60 Hz, which defines the frame rate of a raster scan and can be in the range of video-rate scanning.

The specific numbers provided above are designed for tissue imaging, to illustrate the utility and the performance of the present invention as a way of example. A skilled artisan can utilize model calculations known in the art of confocal theta microscopy to design an angled-dual-axis confocal scanning endoscope in accordance with the present invention, for a given application.

Although the present invention and its advantages have been described in detail, it should be understood that various changes, substitutions, and alternations can be made herein without departing from the principle and the scope of the invention. Accordingly, the scope of the present invention should be determined by the following claims and their legal equivalents.

What is claimed is:

1. An integrated angled-dual-axis confocal scanning system comprising:
   a) a substrate;
   b) a scanning mirror means mechanically coupled to said substrate;
   c) a base-plate, including an optical window disposed adjacent to an object;
   d) a spacer disposed between said substrate and said base-plate, containing a cavity, wherein said cavity comprises first and second reflective surfaces that are facing each other from two opposing sides;
   e) a first optical fiber having first and second ends, for emitting a first illumination beam with a first wavelength from said first end into said cavity;
   f) a second-optical fiber having first and second ends, for receiving a first observation beam at said first end from said cavity; and
   g) an angled-dual-axis focusing means comprising:
      (1) said first and second reflective surfaces; and
      (2) a beam-focusing assembly in optical communication with said first and second reflective surfaces;
      wherein said angled-dual-axis focusing means focuses said first illumination beam to a first focal volume along a first optical axis within said object, and receives said first observation beam emanated from a second focal volume along a second optical axis within said object, whereby said first observation beam is focused onto said first end of said second optical fiber;
      wherein said scanning mirror means is in optical communication with said angled-dual-axis focusing means and said optical window, such that said scanning means receives said first illumination beam from said angled-dual-axis focusing means and directs said first illumination beam through said optical window to said first focal volume within said object, wherein said scanning mirror means collects said first observation beam passing through said optical window and passes said first observation beam to said angled-dual-axis focusing means, wherein said first and second optical axes intersect at an angle within said object, whereby said first and second focal volumes intersect synergistically at a confocal overlapping volume, and wherein said scanning mirror means is further capable of pivoting said first illumination and observation beams in such a way that said confocal overlapping volume moves within said object, thereby providing a scan.

2. The integrated angled-dual-axis confocal scanning system of claim 1 wherein said first optical fiber passes through a first side-wall of said cavity, wherein an inner surface of said first side-wall provides said first reflective surface, and wherein said first end of said first optical fiber is in optical communication with said cavity, such that said first illumination beam emitted from said first end of said first optical fiber is impinging upon said second reflective surface.

3. The integrated angled-dual-axis confocal scanning system of claim 1 wherein said second optical fiber passes through a second side-wall of said cavity, wherein an inner surface of said second side-wall provides said second reflective surface, and wherein said first end of said second optical fiber is in optical communication with said cavity, so as to receive said first observation beam reflected from said first reflective surface.

4. The integrated angled-dual-axis confocal scanning system of claim 1 wherein said beam-focusing assembly is mounted onto said base-plate.

5. The integrated angled-dual-axis confocal scanning system of claim 4 wherein said beam-focusing assembly comprises first and second reflective focusing elements, providing said first and second optical axes respectively, wherein said first reflective focusing element is in optical communication with said second reflective surface and said scanning mirror means, and wherein said second reflective focusing element is in optical communication with said first reflective surface and said scanning mirror means.

6. The integrated angled-dual-axis confocal scanning system of claim 5 wherein said either of said first and second reflective focusing elements comprises an element selected from the group consisting of diffractive optical elements, reflective diffraction lenses, holographic optical elements, reflective off-axis binary lenses, and curved mirrors.

7. The integrated angled-dual-axis confocal scanning system of claim 5 wherein said either of said first and second reflective focusing elements is made to be an integral part of said base-plate.

8. The integrated angled-dual-axis confocal scanning system of claim 5 wherein said optical window is disposed between said first and second reflective focusing elements.

9. The integrated angled-dual-axis confocal scanning system of claim 4 wherein said beam-focusing assembly comprises a dual-beam reflective focusing element providing both of said first and second optical axes, wherein said dual-beam reflective focusing element is in optical communication with said first and second reflective surfaces, and said scanning mirror means.

10. The angled-dual-axis confocal scanning system of claim 9 wherein said dual-beam reflective focusing element comprises an element selected from the group consisting of diffractive optical elements, reflective diffraction lenses, reflective off-axis binary lenses, and curved mirrors.

11. The angled-dual-axis confocal scanning system of claim 9 wherein said dual-beam reflective focusing element is an integral part of said base-plate.

12. The angled-dual-axis confocal scanning system of claim 9 wherein said dual-beam reflective focusing element further provides said optical window.

13. The integrated angled-dual-axis confocal scanning system of claim 1 wherein said scanning mirror means comprises a single scanning mirror, wherein said scanning mirror is substantially flat and can rotate about a pivoting axis, and wherein said scanning element pivots said first illumination and observation beams in such a way that said first and second focal volumes remain intersecting synergistically and that said confocal overlapping volume moves along an arc-line within said object, thereby producing an arc-line scan.

14. The integrated angled-dual-axis confocal scanning system of claim 13 wherein said scanning mirror comprises a silicon micro-machined scanning mirror.

15. The integrated angled-dual-axis confocal scanning system of claim 13 wherein said substrate contains a dish-cavity, wherein said scanning mirror is suspended in said dish-cavity by a hinge element, and wherein said hinge element provides said pivoting axis.

16. The integrated angled-dual-axis confocal scanning system of claim 1 wherein said scanning mirror means comprises first and second scanning mirrors, wherein said first and second scanning mirrors are substantially flat and can co-rotate about a common pivoting axis, and wherein said first and second scanning mirrors jointly pivot first illumination and observation beams in such a way that said first and second focal volumes remain intersecting synergistically and that said confocal overlapping volume moves along an arc-line within said object, thereby producing an arc-line scan.

17. The integrated angled-dual-axis confocal scanning system of claim 16 wherein either of said first and second scanning mirrors comprises a silicon micro-machined scanning mirror.

18. The integrated angled-dual-axis confocal scanning system of claim 16 wherein said substrate contains first and second dish-cavities, wherein said first and second scanning mirrors are suspended in said first and second dish-cavities by first and second hinge elements respectively, and wherein said first and second hinge elements are substantially co-linear and thereby provide said common pivoting axis.

19. The integrated angled-dual-axis confocal scanning system of claim 1 wherein said scanning mirror means comprises a bi-axial scanning element, including a gimbaled assembly of a substantially flat scanning mirror and a frame, wherein said scanning mirror can rotate about a first pivoting axis and said frame along with said scanning mirror can rotate about a second pivoting axis, wherein said first and second pivoting axes are substantially orthogonal, and wherein said bi-axial scanning element pivots said first illumination and observation beams in such a way that said first and second focal volumes remain intersecting synergistically and that said confocal overlapping volume moves in a predetermined pattern along an arc-cross-sectional surface within said object, thereby producing an arc-cross-sectional-surface scan.

20. The integrated angled-dual-axis confocal scanning system of claim 19 wherein said scanning mirror comprises a silicon micro-machined scanning mirror.

21. The integrated angled-dual-axis confocal scanning system of claim 19 wherein said substrate contains a dish-cavity, wherein said bi-axial scanning element is suspended in said dish-cavity by a hinge element, and wherein said hinge element provides said second pivoting axis.

22. The integrated angled-dual-axis confocal scanning system of claim 1 wherein said scanning mirror means comprises first and second scanning mirrors, and wherein said first and second scanning mirrors can rotate about first and second pivoting axes respectively.

23. The integrated angled-dual-axis confocal scanning system of claim 22 wherein first and second pivoting axes are substantially parallel and spaced apart, whereby said first and second scanning mirrors can counter-rotate relative to each other, and wherein said first and second scanning mirrors pivot said first illumination and observation beams in such a way that said first and second focal volumes remain intersecting synergistically and that said confocal overlapping volume progressively deepens into said object, thereby producing a vertical-line scan.

24. The integrated angled-dual-axis confocal scanning system of claim 22 wherein either of said first and second scanning mirrors is a silicon micro-machined scanning mirror.

25. The integrated angled-dual-axis confocal scanning system of claim 22 wherein said substrate contains first and second dish-cavities, wherein said first and second scanning mirrors are suspended in said first and second dish-cavities by first and second hinge elements respectively, and wherein said first and second hinge elements provide said first and second pivoting axes respectively.

26. The integrated angled-dual-axis confocal scanning system of claim 1 wherein said scanning mirror means comprise:
  1) a first gimbaled assembly of a first scanning mirror and a first frame, wherein said first scanning mirror can rotate about a first pivoting axis and said first frame along with said first scanning mirror can rotate about a second pivoting axis; and
  2) a second gimbaled assembly of a second scanning mirror and a second frame, wherein said second scanning mirror can rotate about a third pivoting axis and said second frame along with said second scanning mirror can rotate about a fourth pivoting axis.

27. The integrated angled-dual-axis confocal scanning system of claim 26 wherein said second and fourth pivoting axes are substantially co-linear and thereby define a common pivoting axis, wherein said first and third pivoting axes are substantially parallel and spaced apart, each being substantially perpendicular to said common pivoting axis, wherein said first and second scanning mirrors can co-rotate about said common pivoting axis and can further counter-rotate relative to each other about said first and third pivoting axes respectively, and wherein said first and second scanning mirrors pivot said first illumination and observation beams in such a way that said first and second focal volumes remain intersecting synergistically and that said confocal overlapping volume moves in a predetermined pattern along a vertical-cross-sectional plane within said object, thereby producing a vertical-cross-sectional scan.

28. The integrated angled-dual-axis confocal scanning system of claim 27 wherein said first and second frames are provided by a single common frame, and wherein said common frame can rotate about said common pivoting axis.

29. The integrated angled-dual-axis confocal scanning system of claim 28 wherein said substrate contains a dish-cavity, wherein said common frame is suspended in said dish-cavity by a hinge element, and wherein said hinge element provide said common pivoting axis.

30. The integrated angled-dual-axis confocal scanning system of claim 26 wherein said first and third pivoting axes are substantially co-linear and thereby define a common pivoting axis, wherein said second and fourth pivoting axes are substantially parallel and spaced apart, each being substantially perpendicular to said common pivoting axis, wherein said first and second scanning mirrors can co-rotate about said common pivoting axis and can further counter-rotate relative to each other about said second and fourth pivoting axes respectively, and wherein said first and second scanning mirrors pivot said first illumination and observation beams in such a way that said first and second focal volumes remain intersecting synergistically and that said confocal overlapping volume moves in a predetermined pattern along a vertical-cross-sectional plane within said object, thereby producing a vertical-cross-sectional scan.

31. The integrated angled-dual-axis confocal scanning system of claim 26 wherein either of said first and second scanning mirrors comprises a silicon micro-machined scanning mirror.

32. The integrated angled-dual-axis confocal scanning system of claim 26 wherein said substrate contains first and second dish-cavities, wherein said first and second frames are suspended in said first and second dish-cavities by first and second hinge elements respectively, and wherein said first and second hinge elements provide said second and fourth pivoting axes.

33. The integrated angled-dual-axis confocal scanning system of claim 1 wherein said substrate is made of silicon.

34. The integrated angled-dual-axis confocal scanning system of claim 1 wherein said spacer is made of silicon, and wherein said cavity is anisotropically etched into said spacer.

35. The integrated angled-dual-axis confocal scanning system of claim 34 wherein said cavity comprises first and second side-walls, wherein said first and second side-walls bear first and second V-grooves, whereby said first and second optical fibers pass through said first and second V-grooves respectively, and wherein respective inner surfaces of said first and second side-walls provide said first and second reflective surfaces respectively.

36. The integrated angled-dual-axis confocal scanning system of claim 35 wherein each of said first and second reflective surfaces has a predetermined and precise orientation.

37. The integrated angled-dual-axis confocal scanning system of claim 1 wherein said base-plate is made of fused silica.

38. The integrated angled-dual-axis confocal scanning system of claim 1 wherein said beam-focusing assembly constitutes an integral part of said base-plate.

39. The integrated angled-dual-axis confocal scanning system of claim 1 wherein said optical window is an integral part of said base-plate.

40. The integrated angled-dual-axis confocal scanning system of claim 1 wherein said beam-focusing assembly and said optical window are provided by a composite optical element, and wherein said composite optical element is mounted onto said base-plate.

41. The integrated angled-dual-axis confocal scanning system of claim 1 wherein said spacer and said base-plate form an integral body.

42. The integrated angled-dual-axis confocal scanning system of claim 1 wherein said scanning mirror means along with said substrate, said spacer and said base-plate form an integral body.

43. The integrated angled-dual-axis confocal scanning system of claim 1 wherein either of said first and second optical fibers comprises an element selected from the group consisting of single-mode fibers and multi-mode fibers.

44. The integrated angled-dual-axis confocal scanning system of claim 1 wherein said first observation beam comprises reflected light emanated from said confocal overlapping volume within said object.

45. The integrated angled-dual-axis confocal scanning system of claim 1 wherein said first observation beam comprises fluorescent light emanated from said confocal overlapping volume within said object.

46. The integrated angled-dual-axis confocal scanning system of claim 1 wherein said first and second focal volumes are substantially diffraction-limited, determined by main lobes of said first illumination beam's point-spread function and said first observation beam's point-spread function.

47. The integrated angled-dual-axis confocal scanning system of claim 46 wherein said confocal overlapping volume is substantially diffraction-limited.

48. The integrated angled-dual-axis confocal scanning system of claim 1 further comprising a second illumination beam with a second wavelength emitted from said first end of said second optical fiber, wherein said second illumination beam is directed along said second optical axis and focused to said second focal volume within said object.

49. The integrated angled-dual-axis confocal scanning system of claim 48 wherein said first and second wavelengths are substantially equal.

50. The integrated angled-dual-axis confocal scanning system of claim 48 wherein each of said first and second wavelengths is in the infrared range.

51. The integrated angled-dual-axis confocal scanning system of claim 48 wherein said first and second wavelengths are not equal.

52. The integrated angled-dual-axis confocal scanning system of claim 51 wherein said first wavelength is in the infrared range, and said second wavelength-is in the visible range.

53. The integrated angled-dual-axis confocal scanning system of claim 51 wherein each of said first wavelength and said second wavelength is in the infrared range.

54. The integrated angled-dual-axis confocal scanning system of claim 48 wherein a combination of said first and second illumination beams provides excitation for producing a two-color two-photon (2C2P) fluorescence light within said confocal overlapping volume in said object, and wherein a reciprocal of the wavelength of said two-color two-photon fluorescence light is substantially equal to a sum of respective reciprocals of said first and second wavelengths.

55. The integrated angled-dual-axis confocal scanning system of claim 48 wherein a second observation beam emanated from said first focal volume within said object is collected along said first optical axis and directed onto said first end of said first optical fiber.

56. The integrated angled-dual-axis confocal scanning system of claim 55 wherein either of said first and second observation beams comprises two-photon fluorescence light emanated from said confocal overlapping volume within said object, and wherein a reciprocal of the wavelength of said two-photon fluorescence light is substantially equal to a sum of respective reciprocals of said first and second wavelengths.

57. The integrated angled-dual-axis confocal scanning system of claim 55 wherein said first observation beam comprises a reflected light with said first wavelength.

58. The integrated angled-dual-axis confocal scanning system of claim 55 wherein said second observation beam comprises a reflected light with said second wavelength.

59. The integrated angled-dual-axis confocal scanning system of claim 48 further comprising an auxiliary focusing means, and wherein said auxiliary focusing means collects a third observation beam emanated from said confocal overlapping volume within said object and directs said third observation beam onto an input end of a third optical fiber.

60. The integrated angled-dual-axis confocal scanning system of claim 59 wherein said auxiliary focusing means is mounted onto said base-plate, and wherein said third optical fiber is coupled to said substrate, whereby said input end of said third optical fiber is in optical communication with said cavity and receives said third observation beam from said auxiliary focusing means.

61. The integrated angled-dual-axis confocal scanning system of claim 59 wherein each of said first and second optical fibers is a single-mode fiber, and wherein said third optical fiber is a multi-mode fiber operating at a wavelength associated with fluorescence light of at least one type selected from the group consisting of single-photon fluorescence, one-color two-photon fluorescence, and two-color two-photon fluorescence.

62. The integrated angled-dual-axis confocal scanning system of claim 48 further comprising an auxiliary focusing means, and wherein said auxiliary focusing means collects a third observation beam emanated from said confocal overlapping volume within said object and directs said third observation beam onto an optical detector in optical communication with said auxiliary focusing means.

63. The integrated angled-dual-axis confocal scanning system of claim 62 wherein said auxiliary focusing means is mounted on said base-plate, wherein said optical detector is coupled to said substrate, whereby said optical detector is in optical communication with said cavity and receives said third observation beam from said auxiliary focusing means.

64. The integrated angled-dual-axis confocal scanning system of claim 1 further comprising a first light source optically coupled to said second end of said first optical fiber, providing said first illumination beam.

65. The integrated angled-dual-axis confocal scanning system of claim 64 wherein said first light source comprises an element selected from the group consisting of fiber lasers, semiconductor lasers, and diode-pumped solid state lasers.

66. The integrated angled-dual-axis confocal scanning system of claim 64 further comprising an optical detector optically coupled to said second end of said second optical fiber.

67. The integrated angled-dual-axis confocal scanning system of claim 64 further comprising a second light source optically coupled to said second end of said second optical fiber, providing a second illumination beam.

68. The integrated angled-dual-axis confocal scanning system of claim 67 wherein said first light source is optically coupled to said first optical fiber by way of a wavelength-selective-beam-splitting means.

69. The integrated angled-dual-axis confocal scanning system of claim 68 further comprising an optical detector, optically coupled to said wavelength-selective-beam-splitting means.

70. The integrated angled-dual-axis confocal scanning system of claim 69 wherein said wavelength-selective-beam-splitting means comprises one or more elements selected from the group consisting of dichroic beam-splitters, dichroic filters, bandpass filters, beam-splitters, spectral filters, and wavelength division multiplexers (WDM).

71. The integrated angled-dual-axis confocal scanning system of claim 69 wherein said wavelength-selective-beam-splitting means comprises a fiber-optic WDM coupler.

72. The integrated angled-dual-axis confocal scanning system of claim 67 wherein said second light source is optically coupled to said second optical fiber by way of a wavelength-selective-beam-splitting means.

73. The integrated angled-dual-axis confocal scanning system of claim 72 further comprising an optical detector, optically coupled to said wavelength-selective-beam-splitting means.

74. The integrated angled-dual-axis confocal scanning system of claim 73 wherein said wavelength-selective-beam-splitting means comprises one or more elements selected from the group consisting of dichroic beam-splitters, dichroic filters, bandpass filters, beam-splitters, spectral filters, and wavelength division multiplexers (WDM).

75. The integrated angled-dual-axis confocal scanning system of claim 73 wherein said wavelength-selective-beam-splitting means comprises a fiber-optic WDM coupler.

76. The integrated angled-dual-axis confocal scanning system of claim 67 wherein either of said first and second light sources comprises an element selected from the group consisting of fiber lasers, semiconductor lasers, diode-pumped solid state lasers, and pulsed lasers.

77. The integrated angled-dual-axis confocal scanning system of claim 67 further comprising an adjustable optical delay device optically coupled to either of said first and second optical fibers, so as to ensure a concurrent spatial and temporal overlap of said first and second illumination beams.

78. A method of constructing a fiber-coupled, integrated angled-dual-axis confocal scanning endoscope, comprising:
   a) mechanically coupling a scanning mirror means to a substrate;
   b) producing a cavity in a spacer, wherein first and second side-walls of said cavity comprise first and second V-grooves respectively, and wherein respective inner surfaces of said first and second side-walls provide first and second reflective surfaces respectively;
   c) equipping a base-plate with first and second reflective focusing elements, and an optical window;
   d) disposing said spacer between said substrate and said base-plate, such that said scanning mirror means is in optical communication with said first and second reflective surfaces, said first and second reflective focusing elements, and said optical window;
   e) passing a first optical fiber into said first side-wall of said cavity by way of said first V-groove, whereby a first end of said first optical fiber is in optical communication with said second reflective surface; and
   f) passing a second optical fiber into said second side-wall of said central cavity by way of said second V-groove, whereby a first end of said second optical fiber is in optical communication with said first reflective surface.

79. The method of claim 78 wherein said substrate is made of silicon.

80. The method of claim 78 further comprising the step of etching a dish-cavity into said substrate, whereby said scanning mirror means is suspended in said dish-cavity by way of a hinge element, and wherein said hinge element provides a pivoting axis about which said scanning mirror means can rotate.

81. The method of claim 78 wherein said spacer is made of silicon, and wherein said cavity along with said first and second V-grooves are produced by way of anisotropically etching, whereby each of said first and second reflective surfaces has a predetermined and precise orientation.

82. The method of claim 78 wherein said base-plate comprises fused silica, wherein said first and second reflective focusing elements are fused onto said base-plate, and wherein a transparent region of said base-plate disposed between said first and second reflective focusing elements provides said optical window.

83. The method of claim 78 wherein said scanning mirror means comprises a silicon micro-machined scanning mirror, wherein said scanning mirror is substantially flat and can rotate about a pivoting axis.

84. The method of claim 78 wherein said scanning mirror means comprises first and second silicon micro-machined scanning mirrors, wherein said first and second scanning mirrors are substantially flat and can co-rotate about a common pivoting axis.

85. The method claim of 78 wherein said scanning mirror means is provided by a bi-axial scanning element, comprising a gimbaled assembly of a scanning mirror and a frame, wherein said scanning mirror can rotate about a first pivoting axis and said frame along with said scanning mirror can rotate about a second pivoting axis, and wherein said first and second pivoting axes are substantially orthogonal.

86. The method of claim 78 wherein said scanning mirror means comprises first and second silicon micro-machined scanning mirrors, wherein said first and second scanning mirrors are substantially flat and can counter-rotate about first and second pivoting axes, and wherein said first and second pivoting axes are substantially parallel and spaced apart.

87. The method of claim 78 wherein said scanning mirror means comprises a first gimbaled assembly of a first scanning mirror and a first frame, and a second gimbaled assembly of a second scanning mirror and a second frame, wherein said first scanning mirror can rotate about a first pivoting axis and said first frame along with said first scanning mirror can rotate about a second pivoting axis, and wherein said second scanning mirror can rotate about a third pivoting axis and said second frame along with said second scanning mirror can rotate about a fourth pivoting axis.

88. The method of claim 87 wherein said first and third pivoting axes are substantially co-linear and thereby define a common pivoting axis, and wherein said second and fourth pivoting axes are substantially parallel and spaced apart, each being substantially orthogonal to said common pivoting axis.

89. The method of claim 87 wherein said second and fourth pivoting axes are substantially co-linear and thereby define a common pivoting axis, and wherein said first and third pivoting axes are substantially parallel and spaced apart, each being substantially orthogonal to said common pivoting axis.

90. The method of claim 87 wherein each of said first and second scanning mirrors is a silicon micro-machined scanning mirror.

91. The method of claim 78 further comprising the step of mounting a third focusing element onto said base-plate, whereby said third focusing element is in optical communication with said optical window.

92. The method of claim 91 further comprising the step of coupling a third optical fiber to said substrate, such that an input end of said third optical fiber is in optical communication with said third focusing element.

93. The method of claim 91 further comprising the step of coupling an optical detector to said substrate, whereby said optical detector is in optical communication with said third focusing element.

94. The method of claim 78 wherein either of said first and second optical fibers is selected from the group consisting of single-mode fibers and multi-mode fibers.

95. A method of scanning an object with an integrated angled-dual-axis confocal scanning microscope, comprising:
   a) directing an illumination beam emitted from a first end of a first optical fiber to a second reflective surface;
   b) passing said illumination beam onto a first reflective focusing element;
   c) sending said illumination beam to a scanning mirror means;
   d) focusing said illumination beam to a first focal volume along a first optical axis within said object;
   e) using said scanning mirror means to collect an observation beam emanated from a second focal volume along a second optical axis within said object, wherein said second optical axis is oriented at an angle with respect to said first optical axis such that said first and second focal volumes intersect synergistically at a confocal overlapping volume;
   f) directing said observation beam to a second focusing element;
   g) passing said observation beam onto a first reflective surface;
   h) focusing said observation beam to a first end of a second optical fiber; and
   i) pivoting said illumination and observation beams by said scanning mirror means, such that said confocal overlapping volume moves within said object, thereby providing a scan of said object.

96. The method of claim 95 wherein said scanning mirror means comprises a single scanning mirror, and wherein said step i) comprises rotating said scanning mirror about a pivoting axis in such a way that an arc-line scan is produced.

97. The method of claim 95 wherein said scanning mirror means comprises first and second scanning mirrors, capable of rotating about a common pivoting axis, and wherein said step i) comprises co-rotating said first and second scanning mirrors about said common pivoting axis in such a way that an arc-line scan is produced.

98. The method of claim 95 wherein said scanning mirror means comprises first and second scanning mirrors, capable of rotating respectively about first and second pivoting axes that are substantially parallel and spaced apart, and wherein said step i) comprises counter-rotating said first and second scanning mirrors relative to each other about said first and second pivoting axes in such a way that a vertical-line scan is produced.

99. The method of claim 95 wherein said scanning mirror means comprises a bi-axial scanning element, capable of rotating about first and second pivoting axes respectively, wherein said first and second pivoting axes are substantially orthogonal, and wherein said step i) comprises rotating said bi-axial scanning element about said first and second pivoting axes respectively in such a way that an arc-cross-sectional-surface scan is produced.

100. The method of claim 95 wherein said scanning mirror means comprises first and second bi-axial scanning elements, wherein said first bi-axial scanning element is capable of rotating about first and second pivoting axes respectively, and wherein said second bi-axial scanning element is capable of rotating about third and fourth pivoting axes respectively.

101. The method of claim 100 wherein said second and fourth pivoting axes are substantially co-linear and thereby define a common pivoting axis, wherein said first and third pivoting axes are substantially parallel and spaced apart, and wherein said step i) comprises co-rotating said first and second bi-axial scanning elements about said common pivoting axis and further counter-rotating said first and second bi-axial scanning elements about said first and third pivoting axes in a predetermined fashion, whereby a vertical-cross-sectional scan is produced.

* * * * *

UNITED STATES PATENT AND TRADEMARK OFFICE
CERTIFICATE OF CORRECTION

PATENT NO. : 6,414,779 B1
DATED : July 2, 2002
INVENTOR(S) : Mandella et al.

It is certified that error appears in the above-identified patent and that said Letters Patent is hereby corrected as shown below:

<u>Title page,</u>
Item [73], should read:
-- [73] Assignee: Optical Biopsy Technologies, Inc.,
San Jose, CA (US) --

Signed and Sealed this

Fifth Day of November, 2002

Attest:

Attesting Officer

JAMES E. ROGAN
*Director of the United States Patent and Trademark Office*